United States Patent [19]
Kellogg et al.

[11] Patent Number: 6,143,248
[45] Date of Patent: *Nov. 7, 2000

[54] CAPILLARY MICROVALVE

[75] Inventors: Gregory Kellogg, Somerville; Stephen G. Kieffer-Higgins, Dorchester; Alec Mian, Cambridge, all of Mass.

[73] Assignee: Gamera Bioscience Corp., Medford, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/910,726

[22] Filed: Aug. 12, 1997

Related U.S. Application Data
[60] Provisional application No. 60/023,756, Aug. 12, 1996.

[51] Int. Cl.$^7$ ............................................. G01N 9/30
[52] U.S. Cl. .................. 422/72; 422/64; 422/67; 422/103; 436/45
[58] Field of Search ................. 422/64, 67, 72, 422/103; 436/45

[56] References Cited

U.S. PATENT DOCUMENTS

| | | |
|---|---|---|
| 3,679,367 | 7/1972 | Negersmith et al. . |
| 3,713,062 | 1/1973 | Butler et al. . |
| 3,952,116 | 4/1976 | Trenkler et al. . |

(List continued on next page.)

FOREIGN PATENT DOCUMENTS

| | | |
|---|---|---|
| 322657 | 7/1989 | European Pat. Off. . |
| 0 408 207 A2 | 6/1990 | European Pat. Off. . |
| 417305 | 3/1991 | European Pat. Off. . |
| 305210 | 12/1993 | European Pat. Off. . |
| 616218 | 9/1994 | European Pat. Off. . |
| 0637367B1 | 12/1997 | European Pat. Off. . |
| 1 292 407 | 3/1962 | France . |
| 4410224 | 9/1995 | Germany . |
| 1 307 628 | 2/1973 | United Kingdom . |
| WO 93/22053 | 11/1993 | WIPO . |
| WO 93/22058 | 11/1993 | WIPO . |
| WO 94/26414 | 11/1994 | WIPO . |
| WO 95/33986 | 12/1995 | WIPO . |
| WO 97/08556 | 3/1997 | WIPO . |
| WO 97/21090 | 6/1997 | WIPO . |

OTHER PUBLICATIONS

Anderson, (1968), *Anal. Biochem.*, 28: 545–562.
Renoe et al., (1974), Clin. Chem., 208/8: 955–960.
Burtis et al., (1974), Clin. Chem., 20/8: 932–941.
Fritsche et al., (1975), Clin Biochem., 8: 240–246.
Burtis et al., (1975), Clin. Chem., 21/9: 1225–1233.
Hadjiioannou et al., (1976), Clin. Chem., 22/6: 802–805.
Lee et al., (1978), Clin. Chem., 24/8: 1361–1365.
Cho et al., (1982), Clin. Chem., 28/9: 1961–1965.
Bertrand et al., (1982), Clinica Chimica Acta, 119: 275–284.
Schembri et al., (1992), Clin. Chem., 38/9: 1665–1670.
Columbus et al., (1987), Clin. Chem., 33/9: 1531–1537.
Ekins et all., (1992), Ann. Biol. Clin., 50: 337–353.
Wilding et al., (1994), Clin. Chem., 40/1: 43–47.
Ikada, (1994), Biomaterials, 15/10: 725–736.
Arkles, (1977) Chemtech, 7: 125.
Nakagawa et al., (Apr. 1990), Proc. IEEE Workshop of Micro Electro Mechanical Systems, pp. 89.
Huff et al., (1994), 7$^{th}$ International Conference of Solid-State Sensors and Actuators, pp. 98–101.
Glass et al., (Jun. 1987), Appl. Optics, 26/11: 2181–2187.

(List continued on next page.)

*Primary Examiner*—Jan Ludlow
*Attorney, Agent, or Firm*—McDonnell Boehnen Hulbert & Berghoff

[57] ABSTRACT

The invention provides microvalves for controlling fluid flow from microreservoirs into transfer channels using capillary valving mechanisms for use in apparatus useful for performing microanalytic and microsynthetic analyses and procedures, such as microminiaturization of genetic, biochemical and chemical processes related to analysis, synthesis and purification of biological, chemical, environmental and other compounds.

2 Claims, 25 Drawing Sheets

U.S. PATENT DOCUMENTS

| | | |
|---|---|---|
| 4,030,834 | 6/1977 | Bauer et al. . |
| 4,154,793 | 5/1979 | Guigan . |
| 4,258,740 | 3/1981 | Kaartinen et al. . |
| 4,381,291 | 4/1983 | Ekins . |
| 4,515,889 | 5/1985 | Klose . |
| 4,676,952 | 6/1987 | Edelmann . |
| 4,722,853 | 2/1988 | Batliwalla et al. . |
| 4,729,862 | 3/1988 | Salatiello et al. . |
| 4,745,072 | 5/1988 | Ekins . |
| 4,872,821 | 10/1989 | Weiss . |
| 4,894,204 | 1/1990 | Cornut ................................. 422/72 |
| 4,940,527 | 7/1990 | Kazlauskas et al. . |
| 5,006,749 | 4/1991 | White . |
| 5,061,381 | 10/1991 | Burd . |
| 5,122,284 | 6/1992 | Braynin et al. . |
| 5,160,702 | 11/1992 | Kopf-Sill et al. . |
| 5,171,533 | 12/1992 | Fine et al. . |
| 5,171,695 | 12/1992 | Ekins . |
| 5,173,193 | 12/1992 | Schembri . |
| 5,173,262 | 12/1992 | Burtis et al. . |
| 5,186,844 | 2/1993 | Burd et al. . |
| 5,242,606 | 9/1993 | Braynin et al. . |
| 5,242,803 | 9/1993 | Burtis et al. . |
| 5,252,294 | 10/1993 | Kroy et al. . |
| 5,275,016 | 1/1994 | Chatterjee et al. . |
| 5,304,348 | 4/1994 | Burd et al. . |
| 5,304,487 | 4/1994 | Wilding et al. . |
| 5,368,704 | 11/1994 | Madou et al. . |
| 5,403,415 | 4/1995 | Schembri . |
| 5,409,665 | 4/1995 | Burd . |
| 5,413,732 | 5/1995 | Buhl et al. . |
| 5,426,032 | 6/1995 | Phillips et al. . |
| 5,432,009 | 7/1995 | Tabata et al. . |
| 5,457,053 | 10/1995 | Burd et al. . |
| 5,472,603 | 12/1995 | Schembri . |
| 5,478,750 | 12/1995 | Bernstein et al. . |
| 5,496,520 | 3/1996 | Kelton et al. . |
| 5,518,930 | 5/1996 | Burd . |
| 5,590,052 | 12/1996 | Kopf-Sill et al. . |
| 5,591,643 | 1/1997 | Schembri . |
| 5,599,411 | 2/1997 | Schembri . |
| 5,622,819 | 4/1997 | Herman . |
| 5,624,597 | 4/1997 | Buhl et al. . |
| 5,639,428 | 6/1997 | Cottingham . |
| 5,693,233 | 12/1997 | Schembri . |
| 5,821,116 | 10/1998 | Herman . |

OTHER PUBLICATIONS

Haab et al., (1995), Anal. Chem., 67: 3253–3260.
Dessy, (Oct. 1989), Anal. Chem., 61–19: 1079–1094.
Rosenzweig et al., (1994), Anal. Chem., 66: 1771–1776.
Reijenga et al., (1983), J. Chromatography, 260: 241–254.
Matsue et al., (1990), Rev. Polarogr., 36 :67.
Aoki et al., (1990), Anal. Chem., 62: 2206–2210.
Linliu et al., (1994), Rev. Sci. Instrum., 65/12: 3823–3828.
Esashi et al., (Jul. 1992), Proc. Micro. Electro Mechanical Systems, 11: 43–48.
Ballatine et al., (Jun. 1989), Anal. Chem., 6/11: 704–715.
Collison et al., (Apr. 1990), Anal. Chem., 62/7: 425–437.
Lamture et al., (1994), Nucleic Acids Res., 22/11: 2121–2125.
Foucault, (1991), Anal. Chem., 63: (10) 569A–570A, 572A–579A.
Poole et al., (Jan. 1994), Anal. Chem., 66/1: 27A–37A.
Shoji & Esashi, (1992), Sensors and Actuators, B8:205.
Bor Fuh et al., (1995), Biotechnol. Prog., 11: 14–20.
Heineman, (1993), App. Biochem. Biotech., 41: 87–97.
Patent Abstracts of Japan, (Jan. 1992), vol. 40, No. 9, pp. 1805–1809.
Arquint et al., (Sep. 1994), Clinical Chemistry, vol. 40, No. 9, pp. 1805–1809.
Blackburn et al., (1991), Clin. Chem., 37: 1534–1539.

Pressure = Po + $\frac{2\gamma}{r}$

Po = Vapor Pressure

TIME SEQUENCE:

$F < F^*$ for $R_1 \rightarrow T_1$: No Flow.

(1) Increase F to $$F^*(R_1 \rightarrow T_1) < F < F^*(R_2 \rightarrow T_2)$$

→ Flow through T1 into R2.

Allow R2 to fill (2) Increase F to $$F^*(R_2 \rightarrow T_2) < F < F^*(R_3 \rightarrow T_3)$$

→ Flow through T2 into R3.

CAPILLARY MICROVALVE

This application is related to and claims priority from provisional U.S. Patent Application, Serial No. 60/023,756, filed on Aug. 12, 1996, the disclosure of which is incorporated by reference. This application is also related to U.S. patent application Ser. No. 08/761,063, filed Dec. 5, 1996, and International Application No. PCT/US96/19514, filed Dec. 5, 1996, the disclosures of each of which are expressly incorporated herein.

BACKGROUND OF THE INVENTION

1. Field of the Invention

The invention relates to the methods and apparatus for controlling fluid flow in microfluidic systems. In, particular, the invention provides microvalves for controlling fluid flow from microreservoirs into transfer channels using capillary valving mechanisms. The capillary valving mechanisms of the invention are based on changes in cross-sectional area and geometry of orifices, reservoirs and microchannels and surface treatment of reservoirs and channels. Specific embodiments of the microvalves of the invention are provided to control fluid flow in microchip-based chemical Microsystems using pumping means and in centrifugal rotors and microplatforms as disclosed, for example in International Application WO97/21090. This invention provides microvalving means for use in apparatus useful for performing microanalytic and microsynthetic analyses and procedures, such as microminiaturization of genetic, biochemical and chemical processes related to analysis, synthesis and purification of biological, chemical, environmental and other compounds.

2. Summary of the Related Art

In the field of medical, biological and chemical assays, mechanical and automated fluid handling systems and instruments are known in the prior art.

U.S. Pat. No. 4,279,862, issued Jul. 21, 1981 to Bertaudiere et al. disclose a centrifugal photometric analyzer.

U.S. Pat. No. 4,381,291, issued Apr. 26, 1983 to Ekins teach analytic measurement of free ligands.

U.S. Pat. No. 4,515,889, issued May 7, 1985 to Klose et al. teach automated mixing and incubating reagents to perform analytical determinations.

U.S. Pat. No. 4,676,952, issued Jun. 30, 1987 to Edelmann et al. teach a photometric analysis apparatus.

U.S. Pat. No. 4,745,072, issued May 17, 1998 to Ekins discloses immunoassay in biological fluids.

U.S. Pat. No. 5,061,381, issued Oct. 29, 1991 to Burd discloses a centrifugal rotor for performing blood analyses.

U.S. Pat. No. 5,122,284, issued Jun. 16, 1992 to Braynin et al. discloses a centrifugal rotor comprising a plurality of peripheral cuvettes.

U.S. Pat. No. 5,160,702, issued Nov. 3, 1993 to Kopf-Sill and Zuk discloses rotational frequency-dependent "valves" using capillary forces and siphons, dependent on "wettability" of liquids used to prime said siphon.

U.S. Pat. No. 5,171,695, issued Dec. 15, 1992 to Ekins discloses determination of analyte concentration using two labeling markers.

U.S. Pat. No. 5,173,193, issued Dec. 22, 1992 to Schembri discloses a centrifugal rotor for delivering a metered amount of a fluid to a receiving chamber on the rotor.

U.S. Pat. No. 5,242,803, issued Sep. 7, 1993 to Burtis et al. disclose a rotor assembly for carrying out an assay.

U.S. Pat. No. 5,409,665, issued Apr. 25, 1995 to Burd discloses a cuvette filling in a centrifuge rotor.

U.S. Pat. No. 5,413,009, issued Jul. 11, 1995 to Ekins discloses a method for analyzing analytes in a liquid.

U.S. Pat. No. 5,472,603, issued Dec. 5, 1995 to Schembri discloses an analytical rotor comprising a capillary passage having an exit duct wherein capillary forces prevent fluid flow at a given rotational speed and permit flow at a higher rotational speed.

Anderson, 1968, *Anal. Biochem.* 28: 545–562 teach a multiple cuvette rotor for cell fractionation.

Renoe et al., 1974 *Clin. Chem.* 20: 955–960 teach a "minidisc" module for a centrifugal analyzer.

Burtis et al., 1975, *Clin. Chem.* 20: 932–941 teach a method for a dynamic introduction of liquids into a centrifugal analyzer.

Fritsche et al., 1975, *Clin. Biochem.* 8: 240–246 teach enzymatic analysis of blood sugar levels using a centrifugal analyzer.

Burtis et al., 1975, *Clin Chem.* 21: 1225–1233 teach a multipurpose optical system for use with a centrifugal analyzer.

Hadjiioannou et al., 1976, *Clin. Chem.* 22: 802–805 teach automated enzymatic ethanol determination in biological fluids using a miniature centrifugal analyzer.

Lee et al., 1978, *Clin. Chem.* 24: 1361–1365 teach a automated blood fractionation system.

Cho et al., 1982, *Clin. Chem.* 28: 1956–1961 teach a multichannel electrochemical centrifugal analyzer.

Bertrand et al., 1982, *Clinica Chimica Acta* 119: 275–284 teach automated determination of serum 5'-nucleotidase using a centrifugal analyzer.

Schembri et al., 1992, *Clin Chem.* 38: 1665–1670 teach a portable whole blood analyzer.

Walters et al., 1995, *Basic Medical Laboratory Technologies,* 3rd ed., Delmar Publishers: Boston teach a variety of automated medical laboratory analytic techniques.

Recently, microannlytical devices for performing select reaction pathways have been developed.

U.S. Pat. No. 5,006,749, issued Apr. 9, 1991 to White disclose methods apparatus for using ultrasonic energy to move microminiature elements.

U.S. Pat. No. 5,252,294, issued Oct. 12, 1993 to Kroy et al. teach a micromechanical structure for performing certain chemical microanalyses.

U.S. Pat. No. 5,304,487, issued Apr. 19, 1994 to Wilding et al. teach fluid handling on microscale analytical devices.

U.S. Pat. No. 5,368,704, issued Nov. 29, 1994 to Madou et al. teach microelectrochemical valves.

International Application, Publication No. WO93/22053, published Nov. 11, 1993 to University of Pennsylvania disclose microfabricated detection structures.

International Application, Publication No. WO93/22058, published Nov. 11, 1993 to University of Pennsylvania disclose microfabricated structures for performing polynucleotide amplification.

Columbus et al., 1987, *Clin. Chem.* 33: 1531–1537 teach fluid management of biological fluids.

Ekins et al., 1994 *Ann. Biol. Clin.* 50: 337–353 teach a multianalytic microspot immunoassay.

Wilding et al., 1994, *Clin. Chem.* 40: 43–47 disclose manipulation of fluids on straight channels micromachined into silicon.

One drawback in the prior art microanalytical methods and apparati has been the difficulty in designing systems for moving fluids on microchips through channels and reservoirs having diameters in the 10–100 μm range. Microfluidic systems require precise and accurate control of fluid flow and valving to control chemical reactions and analyte detection. Conventional pumping and valving mechanisms have been difficult to incorporate into microscale structures due to inherent conflicts-of-scale. These conflicts of scale arise in part due to the fact that molecular interactions arising out of mechanical components of such valves, which are negligible in large (macroscopic) scale devices, become very significant for devices built on a microscopic scale.

One such phenomenon associated with microscale devices is termed "stiction". Stiction is functionally defined as the adhesion of two components under static conditions. Stiction may be due to a variety of causes, such as electrostatic charge transfer, chemical or hydrogen bonding or precipitation of adherent chemicals while the parts are in contact. In order to overcome stiction, a disproportionately large amount of mechanical or electrical energy must be applied. However, the application of such energy and the accompanying force on the microvalve can completely overwhelm the delicate structural and electrical features of the devices. In addition, the manufacture of complex valves and associated circuitry is challenging and results in prohibitively high manufacturing costs.

Systems that use centripetal force to effect fluid movement in microstructures address the need for a pumping mechanism to effect fluid flow, but do not solve these valving needs. The present invention permits precise and accurate control of valving, flow and metering of fluids in microstructural platforms, including both microchip-based and centrifugal microplatform-based technologies, using structures that take advantage of surface tension and capillarity.

SUMMARY OF THE INVENTION

The present invention provides centrifugal rotors and microsystems platforms, as disclosed in International Application WO97/21090 having solid-state microvalves that control fluid flow in the rotor or microsystems platform. The invention provides such microvalves wherein fluid flow on a centrifugal rotor or microsystem platform is motivated by centripetal force of the rotating rotor or platform and controlled by the arrangement, dimensions and surface characteristics of the fluid-handling components (including capillary microchannels and fluid reservoirs) of the rotor or platform. The invention particularly provides arrangements of such fluid-handling components to provide for precise delivery of metered amounts of a fluid, preferably a fluid comprising a biological sample, to a fluid reservoir on the rotor, after application to the rotor of a relatively imprecise or excess amount of said biological sample. The invention also provides arrangement of such fluid-handling components on centrifugal rotors or microsystems platforms wherein a fluid volume contained in one fluid reservoir of the rotor or platform is displaced from the reservoir by centripetally-motivated movement of a second fluid volume from a second fluid reservoir.

In a first embodiment is provided a centrifugal rotor or microsystems platform for providing centripetally-motivated fluid micromanipulation, whereby a precisely metered amount of a fluid sample, most preferably comprising a biological sample, is aliquotted on the rotor or platform from a less precisely applied sample volume. In this embodiment of the invention, said rotor or platform is a rotatable platform, comprising a substrate having a first flat, planar surface and a second flat, planar surface opposite thereto, each surface comprising a center about which the platform is rotated. In said centrifugal rotor or microplatform is provided a first surface that comprises the following components in combination:

1. An entry port comprising a depression in the first surface having a volumetric capacity of about 1 to about 150 μL and that is accessible to an operator for application of a fluid sample, most preferably a fluid comprising a biological sample. The entry port is fluidly connected with
2. A first metering capillary and
3. A second overflow capillary each capillary fluidly connected with the entry port. Each capillary defines a cross-sectional area of about 0.02 mm to about 1 mm in diameter, and each capillary extends radially from the center of the platform, defining a first end proximally arrayed towards the center of the platform and fluidly connected with the entry port, and a second end distally arrayed from the center of the platform, and wherein the proximal end of each capillary defines a curved opening. The first metering capillary also defines a volume of the fluid when filled from the opening at the first end of the capillary to the second end of the capillary. Each capillary comprises a material that is "wettable" by the fluid, particularly fluid comprising a biological sample, so that fluid placed into contact with the first end of each capillary at the entry port flows by capillary action on the rotor or platform at rest (i.e., without rotation of the rotor or the platform) through each capillary to the second end of the capillary, which forms a capillary junction that prevents further fluid flow in the absence of the application of centripetal force applied by rotating the rotor or platform.

The first metering capillary is further fluidly connected with

4. A first fluid chamber having a depth in the surface of the platform that is equal to or greater than the depth of the metering capillary. The first fluid chamber is positioned radially more distant from the center of the platform than the entry port, and the difference in cross-sectional area between the first metering capillary and the first fluid chamber produces the capillary junction at the second end of the first metering capillary that prevents further fluid flow in the absence of the application of centripetal force applied by rotating the rotor or platform.

The second overflow capillary is further fluidly connected with

5. An overflow chamber having a depth in the surface of the platform equal to or greater than the depth of the overflow capillary. The overflow chamber is positioned radially more distant from the center of the platform than the entry port or the first fluid chamber, and the difference in cross-sectional area between the second overflow capillary and the overflow chamber produces the capillary junction at the second end of the second overflow capillary that prevents further fluid flow in the absence of the application of centripetal force applied by rotating the rotor or platform.

In this arrangement, fluid placed onto the disk at the entry port flows by capillary action to the junction of the metering capillary and the first fluid chamber, and excess fluid flows by capillary action to the junction of the overflow capillary and the overflow chamber. Rotation of the platform at a first rotation speed motivates fluid displacement in the overflow capillary into the overflow chamber but does not fluid displacement in the metering capillary. In this way, rotation of the platform at the first rotational speed drains the fluid from the entry port into the overflow chamber, leaving a precisely defined amount of the fluid in the first metering capillary. Thereafter, rotation of the platform at a second rotation speed that is greater than the first rotational speed motivates fluid displacement of the volume of the fluid in the metering capillary into the first chamber, thereby delivering a precisely-determined amount of the fluid, most preferably a fluid comprising a biological sample, to the first fluid chamber.

In preferred embodiments, the platform also comprises air displacement channels whereby air displaced by fluid movement is vented to the surface of the platform.

In a preferred embodiment, the rotatable platform has a diameter of about 20 mm to about 400 mm. In a preferred embodiment, the entry port is from about 0.25 mm to about 1 mm deep. In a preferred embodiment, the entry port is positioned from about 1 cm to about 20 cm. In a preferred embodiment, the first metering capillary has a cross-sectional dimension of from about 0.02 mm to about 0.75 mm. In a preferred embodiment, the first metering capillary is from about 5 mm to about 100 mm long. In a preferred embodiment, the first metering capillary comprises a volume from about 1 $\mu$L to about 150 $\mu$L. In a preferred embodiment, the first metering capillary is radially extends from about 10 mm to about 200 mm from the center of the platform. In a preferred embodiment, the second overflow capillary has a cross-sectional dimension of from about 0.02 mm to about 0.75 mm. In a preferred embodiment, the second overflow capillary is from about 5 mm to about 100 mm long. In a preferred embodiment, the second overflow capillary is radially extends from about 10 mm to about 200 mm from the center of the platform. In a preferred embodiment, the first fluid chamber is from about 0.25 mm to about 1 mm deep. In a preferred embodiment, the first fluid chamber comprises a volume of about 1 $\mu$L to about 150 $\mu$L. In a preferred embodiment, the first fluid chamber is radially extends from about 15 mm to about 115 mm from the center of the platform. In a preferred embodiment, the first rotational speed is from about 10 rpm to about 500 rpm. In a preferred embodiment, the second rotational speed is from about 100 rpm to about 200 rpm. In a preferred embodiment, a volume of from about 1 $\mu$L to about 150 $\mu$L is delivered to the first fluid chamber at the second rotational speed.

In the practice of the invention is also provided a method for moving a fluid in a microsystem platform of the invention. In this embodiment, the invention provides a method having the steps of 1. Applying an amount of a fluid sample, most preferably a biological fluid sample to the entry port of the rotatable microsystem platform, the sample comprising a volume of about 1 to about 100 $\mu$L. In preferred embodiments, the biological fluid sample is a blood drop.
2. Rotating the platform at a first rotation speed for a time sufficient to displace the fluid in the entry port and the overflow capillary into the overflow chamber.
3. Rotating the platform at a second rotation speed that is greater than the first rotational speed to displace a volume of the fluid sample in the metering capillary into a first fluid chamber. In a preferred embodiment, the first rotational speed is from about 10 rpm to about 500 rpm.

In a preferred embodiment, the second rotational speed is from about 100 rpm to about 200 rpm.

In a preferred embodiment, a volume of from about 1 $\mu$L to about 150 $\mu$L is delivered to the first fluid chamber at the second rotational speed.

In a second embodiment of the invention is provided a centrifugal rotor or Microsystems platform for providing centripetally-motivated fluid micromanipulation, wherein a volume of a fluid sample, most preferably comprising a biological sample, in a fluid chamber of the rotor or platform is approximately completely displaced in the chamber by replacement of the volumetric capacity of the chamber with an amount of a displacement fluid. In such embodiments of the invention, said rotor or platform is a rotatable platform, comprising a substrate having a first flat, planar surface and a second flat, planar surface opposite thereto, each surface comprising a center about which the platform is rotated. In said centrifugal rotor or microplatform is provided a first surface that comprises the following components in combination:

1. An entry port comprising a depression in the first surface having a volumetric capacity of about 1 to about 150 $\mu$L and that is accessible to an operator for application of a fluid sample, most preferably a fluid comprising a biological sample. The entry port is fluidly connected with
2. A first microchannel which defines a cross-sectional area of about 0.02 mm to about 1 mm in diameter that extends radially from the center of the platform and defines a first end proximally arrayed towards the center of the platform and is fluidly connected with the entry port, and a second end distally arrayed from the center of the platform. A capillary junction is formed between the proximal end of the microchannel and the entry port that prevents further fluid flow in the absence of the application of centripetal force applied by rotating the rotor or platform. Fluid placed into contact with the first end of the capillary at the entry port does not flow into the microchannel unless centripetal force is applied to the fluid by rotating the rotor or platform.

The first microchannel is further fluidly connected with

3. A first fluid chamber having a depth in the surface of the platform equal to or greater than the first microchannel and positioned radially more distant from the center of the platform than the entry port. The entry port, microchannel and first fluid chamber are arrayed on the surface of the platform so that rotation of the platform at a first rotational speed motivates displacement of the fluid in the entry port through the first microchannel and into the first fluid chamber.

The rotor or platform further comprises

4. A second fluid chamber containing a volume of a displacement fluid, that is fluidly connected with
5. A second microchannel, wherein the second microchannel extends radially from the center of the platform and defines a first end proximally arrayed towards the center of the platform and a second end distally arrayed from the center of the platform. The second microchannel is fluidly connected with the second fluid chamber at the first end of the microchannel and the second microchannel is fluidly connected with the first fluid chamber at the second end of the microchannel. Rotation of the platform at the first rotation speed does not motivate flow of the displacement fluid through the second microchannel. The second microchannel comprises a material that is not "wettable" by the displacement fluid, so that fluid placed into contact with the first end of the capillary at the second fluid chamber does not flow into the microchannel unless centripetal force is applied to the fluid by rotating the rotor or platform at a higher rotational speed than the first rotational speed. Alternatively, the difference in cross-sectional area of the microchannel and the second fluid chamber is sufficient to form a capillary junction at the first end of the microchannel, so that fluid does not flow into the microchannel unless centripetal force is applied to the fluid by rotating the rotor or platform at a higher rotational speed than the first rotational speed.

The platform further comprises

6. A third fluid chamber comprising a displacement fluid that is fluidly connected with
7. A third microchannel, wherein the third microchannel extends radially from the center of the platform and defines a first end proximally arrayed towards the center of the platform and a second end distally arrayed from the center of the platform, wherein the third microchannel is fluidly connected with the third fluid chamber at the first end of the microchannel and wherein the third microchannel is fluidly connected with the first fluid chamber at the second end of the microchannel. Rotation of the platform at the first rotation speed does not motivate flow of the fluid sample through the third microchannel.

Rotation of the platform at the second rotational speed motivates flow of the displacement fluid from the second fluid chamber, through the second microchannel and into the first fluid chamber, wherein flow of the displacement fluid into the first fluid chamber forces the fluid in the first fluid chamber through the third microchannel and into the third fluid chamber. In preferred embodiments, displacement fluid flow into the first fluid chamber is laminar and without turbulence, that is, the displacement fluid forces the fluid, most preferably a biological sample fluid, out of the first fluid chamber and into the third microchannel without mixing of the sample fluid and the displacement fluid.

In a preferred embodiment, the rotatable platform has a diameter of about 20 mm to about 400 mm. In a preferred embodiment, the entry port is from about 0.25 mm to about 1 mm deep. In a preferred embodiment, the entry port is positioned from about 1 cm to about 20 cm. In a preferred embodiment, each of the fluid chambers is from about 0.25 mm to about 1 mm deep. In a preferred embodiment, each of the fluid chambers comprises a volume of about 1 $\mu$L to about 150 $\mu$L. In a preferred embodiment, each of the fluid chambers radially extends from about 15 mm to about 115 mm from the center of the platform. In a preferred embodiment, the first rotational speed is from about 10 rpm to about 500 rpm. In a preferred embodiment, the second rotational speed is from about 100 rpm to about 2000 rpm. In a preferred embodiment, a volume of from about 1 $\mu$L to about 150 $\mu$L is displaced from the first fluid chamber into the third fluid chamber by laminar displacement fluid flow from the second fluid chamber to the first fluid chamber at the second rotational speed.

In the practice of the invention is also provided a method for moving a fluid in a microsystem platform of the invention. In this embodiment, the invention provides a method having the steps of 1. Applying an amount of a fluid sample, most preferably a biological fluid sample to the entry port of the rotatable microsystem platform, the sample comprising a volume of about 1 to about 1 $\mu$L. In preferred embodiments, the biological fluid sample is a blood drop.
2. Rotating the platform at a first rotation speed for a time sufficient to displace the fluid in the entry port into the first fluid chamber.
3. Rotating the platform at a second rotation speed that is greater than the first rotational speed to displace the displacement fluid through the second microchannel and into the first chamber. The displacement fluid is introduced into the first chamber by laminar flow, wherein the displacement fluid does not mix with the fluid, most preferably a fluid comprising a biological sample, in the first fluid chamber. Movement of the displacement fluid by laminar flow into the first fluid chamber forces the fluid in the first fluid chamber, most preferably a fluid comprising a biological sample, through the third microchannel and into the third fluid chamber.

In a third embodiment is provided a centrifugal rotor or microsystems platform for providing centripetally-motivated fluid micromanipulation, whereby a precisely metered amount of a fluid sample, most preferably comprising a biological sample, is aliquotted on the rotor or platform from a less precisely applied sample volume, and wherein a volume of a fluid sample, most preferably comprising a biological sample, in a fluid chamber of the rotor or platform is approximately completely displaced in the chamber by replacement of the volumetric capacity of the chamber with an amount of a displacement fluid. In such embodiments of the invention, said rotor or platform is a rotatable platform, comprising a substrate having a first flat, planar surface and a second flat, planar surface opposite thereto, each surface comprising a center about which the platform is rotated. In said centrifugal rotor or microplatform is provided a first surface that comprises the following components in combination:

1. An entry port comprising a depression in the first surface having a volumetric capacity of about 1 to about 150 $\mu$L and that is accessible to an operator for application of a fluid sample, most preferably a fluid comprising a biological sample. The entry port is fluidly connected with
2. A first metering capillary and
3. A second overflow capillary each capillary fluidly connected with the entry port. Each capillary defines a cross-sectional area of about 0.02 mm to about 1 mm in diameter, and each capillary extends radially from the center of the platform, defining a first end proximally arrayed towards the center of the platform and fluidly connected with the entry port, and a second end distally arrayed from the center of the platform, and wherein the proximal end of each capillary defines a curved opening. The first metering capillary also defines a volume of the fluid when filled from the opening at the first end of the capillary to the second end of the capillary. Each capillary comprises a material that is "wettable" by the fluid, particularly fluid comprising a biological sample, so that fluid placed into contact with the first end of each capillary at the entry port flows by capillary action on the rotor or platform at rest (i.e., without rotation of the rotor or the platform) through each capillary to the second end of the capillary, which forms a capillary junction that prevents further fluid flow in the absence of the application of centripetal force applied by rotating the rotor or platform.

The first metering capillary is further fluidly connected with

4. A first fluid chamber having a depth in the surface of the platform that is equal to or greater than the depth of the metering capillary. The first fluid chamber is positioned radially more distant from the center of the platform than the entry port, and the difference in cross-sectional area between the first metering capillary and the first fluid chamber produces the capillary junction at the second end of the first metering capillary that prevents further fluid flow in the absence of the application of centripetal force applied by rotating the rotor or platform.

The second overflow capillary is further fluidly connected with

5. An overflow chamber having a depth in the surface of the platform equal to or greater than the depth of the overflow capillary. The overflow chamber is positioned radially more distant from the center of the platform than the entry port or the first fluid chamber, and the difference in cross-sectional area between the second overflow capillary and the overflow chamber produces the capillary junction at the second end of the second overflow capillary that prevents further fluid flow in the absence of the application of centripetal force applied by rotating the rotor or platform.

In this arrangement, fluid placed onto the disk at the entry port flows by capillary action to the junction of the metering capillary and the first fluid chamber, and excess fluid flows by capillary action to the junction of the overflow capillary and the overflow chamber. Rotation of the platform at a first rotation speed motivates fluid displacement in the overflow capillary into the overflow chamber but does not fluid displacement in the metering capillary. In this way, rotation of the platform at the first rotational speed drains the fluid from the entry port into the overflow chamber, leaving a precisely defined amount of the fluid in the first metering capillary. Thereafter, rotation of the platform at a second rotation speed that is greater than the first rotational speed motivates fluid displacement of the volume of the fluid in the metering capillary into the first chamber, thereby delivering a precisely-determined amount of the fluid, most preferably a fluid comprising a biological sample, to the first fluid chamber.

The rotor or platform also comprises

6. A second fluid chamber containing a volume of a displacement fluid, that is fluidly connected with 7. A first microchannel, wherein the first microchannel extends radially from the center of the platform and defines a first end proximally arrayed towards the center of the platform and a second end distally arrayed from the center of the platform. The second microchannel is fluidly connected with the second fluid chamber at the first end of the microchannel and the microchannel is fluidly connected with the first fluid chamber at the second end of the microchannel. Rotation of the platform at the firs or second rotational speeds does not motivate flow of the displacement fluid through the first microchannel. A capillary junction is formed between the proximal end of the first microchannel and the second fluid chamber that prevents displacement fluid flow in the absence of the application of centripetal force applied by rotating the rotor or platform at a higher rotational speed than the first or second rotational speed.

The platform further comprises

8. A third fluid chamber that is fluidly connected with

9. A second microchannel, wherein the second microchannel extends radially from the center of the platform and defines a first end proximally arrayed towards the center of the platform and a second end distally arrayed from the center of the platform, wherein the second microchannel is fluidly connected with the third fluid chamber at the first end of the microchannel and wherein the microchannel is fluidly connected with the first fluid chamber at the second end of the microchannel. Rotation of the platform at the first or second rotation speeds does not motivate flow of the fluid sample in the first fluid chamber through the second microchannel.

Rotation of the platform at the third rotational speed motivates flow of the displacement fluid from the second fluid chamber, through the second microchannel and into the first fluid chamber, wherein flow of the displacement fluid into the first fluid chamber forces the fluid in the first fluid chamber through the third microchannel and into the third fluid chamber. In preferred embodiments, displacement fluid flow into the first fluid chamber is laminar, that is, the displacement fluid forces the fluid, most preferably a biological sample fluid, out of the first fluid chamber and into the third microchannel without mixing of the sample fluid and the displacement fluid.

In preferred embodiments, the platform also comprises air displacement channels whereby air displaced by fluid movement is vented to the surface of the platform.

In the practice of the invention is also provided a method for moving a fluid in a microsystem platform of the invention. In this embodiment, the invention provides a method having the steps of 1. Applying an amount of a fluid sample, most preferably a biological fluid sample to the entry port of the rotatable microsystem platform, the sample comprising a volume of about 1 to about 100 $\mu$L. In preferred embodiments, the biological fluid sample is a blood drop.
2. Rotating the platform at a first rotation speed for a time sufficient to displace the fluid in the entry port and the overflow capillary into the overflow chamber.
3. Rotating the platform at a second rotation speed that is greater than the first rotational speed to displace a volume of the fluid sample in the metering capillary into a first fluid chamber.
4. Rotating the platform at a third rotation speed that is greater than the first and second rotational speeds to displace the displacement fluid through the first microchannel and into the first chamber. The displacement fluid is introduced into the first chamber by laminar flow, wherein the displacement fluid does not mix with the fluid, most preferably a fluid comprising a biological sample, in the first fluid chamber. Movement of the displacement fluid by laminar flow into the first fluid chamber forces the fluid in the first fluid chamber, most preferably a fluid comprising a biological sample, through the second microchannel and into the third fluid chamber.

Preferred embodiments are as above for the metering and displacement embodiments considered separately.

In a fourth embodiment of the invention is provided a centrifugal rotor or Microsystems platform for providing centripetally-motivated fluid micromanipulation, wherein a volume of a fluid sample, most preferably comprising a biological sample, in a first fluid chamber of the rotor or platform is delivered in a stream of droplets into a second fluid chamber on the rotor or platform. In such embodiments of the invention, said rotor or platform is a rotatable platform, comprising a substrate having a first flat, planar surface and a second flat, planar surface opposite thereto, each surface comprising a center about which the platform is rotated. In said centrifugal rotor or microplatform is provided a first surface that comprises the following components in combination:

1. An entry port comprising a depression in the first surface having a volumetric capacity of about 1 to about 150 µL and that is accessible to an operator for application of a fluid sample, most preferably a fluid comprising a biological sample. The entry port is fluidly connected with
2. A first microchannel which defines a cross-sectional area of about 0.02 mm to about 1 mm in diameter that extends radially from the center of the platform and defines a first end proximally arrayed towards the center of the platform and is fluidly connected with the entry port, and a second end distally arrayed from the center of the platform. The first microchannel is further fluidly connected with
3. A first fluid chamber having a depth in the surface of the platform equal to or greater than the first microchannel and positioned radially more distant from the center of the platform than the entry port. Rotation of the platform at a first rotational speed motivates displacement of the fluid in the entry port through the first microchannel and into the first fluid chamber.

The platform further comprises

4. A second microchannel, wherein the second microchannel extends radially from the center of the platform and defines a first end proximally arrayed towards the center of the platform and a second end distally arrayed from the center of the platform. The second microchannel is fluidly connected with the first fluid chamber at the first end of the microchannel and the second microchannel is fluidly connected at the second end of the microchannel with
5. A second fluid chamber having a depth in the surface of the platform equal to or greater than the second microchannel and positioned radially more distant from the center of the platform than the first fluid chamber.

The second end of the second microchannel comprises a surface that is non-wetting, or alternatively the second end of the second microchannel defines an opening into the second fluid reservoir. Rotation of the platform at the first rotation speed does not motivate flow of the displacement fluid through the second microchannel. Rotation of the platform at a second rotational speed that is greater than the first rotational speed motivates flow of the fluid from the first fluid chamber, through the second microchannel and into the second fluid chamber. As a consequence of the properties of the second end of the second microchannel, flow of the fluid into the second fluid chamber comprises a stream of droplets from about 0.1 to about 10 µL in volume. In addition, each of the microchannels and the fluid chambers also comprise air displacement channels whereby air displaced by fluid movement is vented to the surface of the platform.

In the practice of the invention is also provided a method for moving a fluid in a microsystem platform of the invention. In this embodiment, the invention provides a method having the steps of 1. Applying an amount of a fluid sample, most preferably a biological fluid sample to the entry port of the rotatable microsystem platform, the sample comprising a volume of about 1 to about 100 µL. In preferred embodiments, the biological fluid sample is a blood drop.
2. Rotating the platform at a first rotation speed for a time sufficient to displace the fluid in the entry port into the first fluid chamber.
3. Rotating the platform at a second rotation speed that is greater than the first rotational speed to displace the displacement fluid through the second microchannel and into the second fluid chamber wherein the flow of the fluid from the second end of the second microchannel into the second fluid chamber comprises a stream of droplets having a volume of from about 0.1 µL to about 10 µL.

It is an advantage of the centrifugal rotors and microsystems platforms of the invention that an imprecise amount of a fluid comprising a biological sample can be applied to the rotor or platform and a precise volumetric amount of the biological sample is delivered to a fluid reservoir comprising a reaction vessel or other component of the rotor of platform for performing chemical, biochemical, immunological or other analyses. It is an advantage of the centrifugal rotors and microsystems platforms of the invention that metering of said precise amount of a biological fluid sample, for example, a drop of blood, is provided as an intrinsic property of the metering capillary channel of the rotor or platform, thereby avoiding variability introduced by centripetal metering of the sample into a reaction reservoir. It is a further advantage of the centrifugal rotors and microsystems platforms of the invention that an operator can avoid having to precisely measure an amount of a fluid comprising a biological sample for application to the rotor or microsystem platform, thereby permitting end-users, including consumers, having a lower level of sophistication to use a medically diagnostic or other embodiment of the rotor or microsystem platform of the invention.

It is an advantage of the centrifugal rotors and microsystems platforms of the invention that fluid movement into and out of fluid reservoirs on the rotor or platform is precisely determined by displacement of a first fluid, such as biological sample, from a fluid reservoir by a second fluid contained in a second reservoir on the rotor or platform. It is also an advantage of the centrifugal rotors and Microsystems platforms of the invention that approximately complete replacement of the volumetric capacity of a first reservoir can be achieved by using fluid displacement as disclosed herein, thereby providing for maximum recovery of a first fluid sample upon displacement by a second fluid, or maximum delivery and replacement of the first fluid by the second fluid. This aspect of the invention is advantageous for providing sequential chemical or biochemical reaction steps wherein mixing of the reagents is not desired.

It is a further advantage of the centrifugal rotors and microsystems platforms of the invention that fluid movement into and out of fluid reservoirs on the rotor or platform is accomplished by providing a stream of droplets at the end of a microchannel or capillary, wherein fluid is delivered into a fluid chamber thereby. Such embodiments are particularly advantageous for enriching or concentrating a mixture comprising particulate material, advantageously including cells, in a method for centrifugally separating or concentrating such particulates in a mixture from the solution in which the particulates are suspended. Such embodiments are also particularly advantageous where thorough mixing of the fluid in the chamber is required.

Specific preferred embodiments of the present invention will become evident from the following more detailed description of certain preferred embodiments and the claims.

DETAILED DESCRIPTION OF THE INVENTION

Figure 1A:
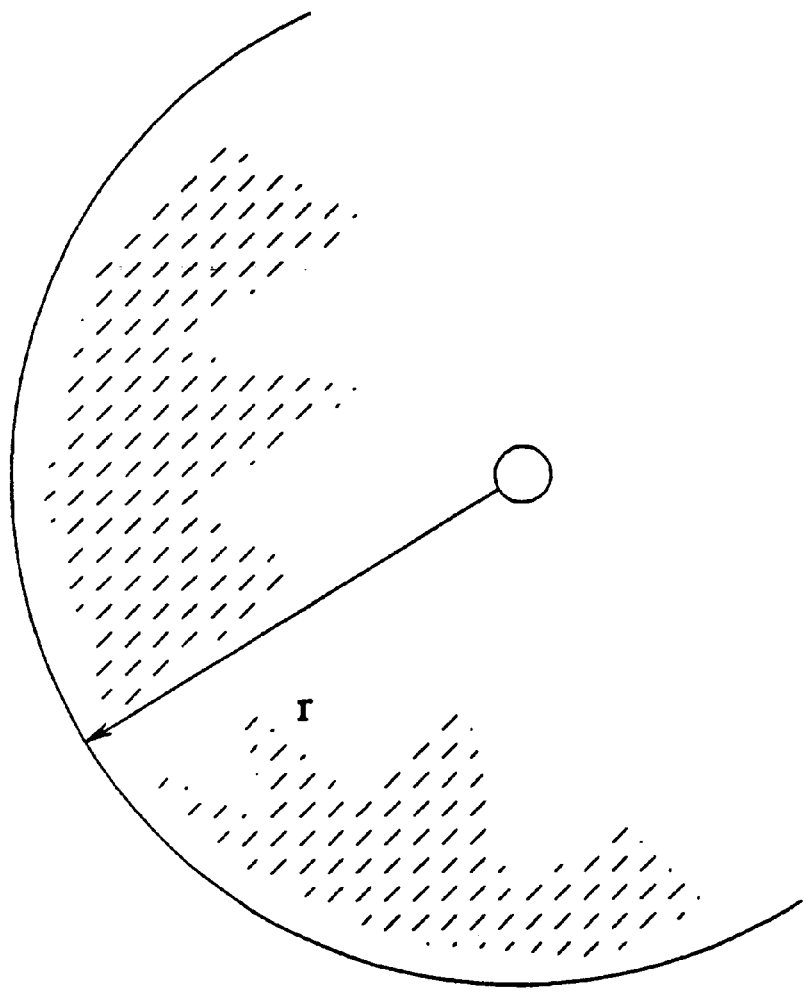
FIG. 1a illustrates the relationship between pressure and position on a rotating platform of the invention.

For the purposes of this invention, the term "sample" will be understood to encompass any chemical or particulate species of interest, either isolated or detected as a constituent of a more complex mixture, or synthesized from precursor species.

For the purposes of this invention, the term "fluidly connected" will be understood to mean micromanipulation apparatus" is intended to include analytical centrifuges and rotors, microscale centrifugal separation apparati, and most particularly the Microsystems platforms and disk handling apparati of International Application No. WO97/21090.

For the purposes of this invention, the terms "capillary", "microcapillary" and "microchannel" will be understood to be interchangeable and to be constructed of either wetting or non-wetting materials where appropriate.

For the purposes of this invention, the term "fluid chamber" will be understood to mean a defined volume on a rotor or Microsystems platform of the invention comprising a fluid.

For the purposes of this invention, the term "entry port" will be understood to mean a defined volume on a rotor or microsystems platform of the invention comprising a means for applying a fluid to the rotor or platform.

For the purposes of this invention, the term "capillary junction" will be understood to mean a junction of two components wherein one or both of the lateral dimensions of the junction are larger than the corresponding dimensions the capillary. In wetting or wettable systems, the such junctions are where the valving occurs, because fluid flow through the capillaries is stopped at such junctions. In non-wetting or non-wettable junctions, the exit from the chamber or reservoir is where the capillary junction occurs. In general, it will be understood that capillary junctions are formed when the dimensions of the components change from a small diameter (such as a capillary) to a larger diameter (such as a chamber) in wetting systems, in contrast to non-wettable systems, where capillary junctions form when the dimensions of the components change from a larger diameter (such as a chamber) to a small diameter (such as a capillary).

For the purposes of this invention, the term "biological sample" or "biological fluid sample" will be understood to mean any biologically-derived analytical sample, including but not limited to blood, plasma, serum, lymph, saliva, tears, cerebrospinal fluid, urine, sweat, plant and vegetable extracts, semen, and ascites fluid.

For the purposes of this invention, the term "air displacement channels" will be understood to include ports in the surface of the platform that are contiguous with the components (such as chambers and reservoirs) on the platform, and that comprise vents and microchannels that permit displacement of air from components of the platforms and rotors by fluid movement.

For the purposes of this invention, the term "capillary action" will be understood to mean fluid flow in the absence of rotational motion or centripetal force applied to a fluid on a rotor or platform of the invention.

For the purposes of this invention, the term "capillary microvalve" will be understood to mean a capillary comprising a capillary junction whereby fluid flow is impeded and can be motivated by the application of pressure on a fluid, typically by centripetal force created by rotation of the rotor or platform of the invention.

The microplatforms of the invention (preferably and hereinafter collectively referred to as "disks"; for the purposes of this invention, the terms "microplatform", "Microsystems platform" and "disk" are considered to be interchangeable), are provided to comprise one or a multiplicity of microsynthetic or microanalytic systems. Such microsynthetic or microanalytic systems in turn comprise combinations of related components as described in further detail herein that are operably interconnected to allow fluid flow between components upon rotation of the disk. These components can be fabricated as described below either integral to the disk or as modules attached to, placed upon, in contact with or embedded in the disk. The invention also comprises a micromanipulation device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention.

User interface means (such as a keypad and a display) are also provided, as further described in International Application WO97/21090.

Fluid (including reagents, samples and other liquid components) movement is controlled by centripetal acceleration due to rotation of the platform. The magnitude of centripetal acceleration required for fluid to flow at a rate and under a pressure appropriate for a particular microsystem is determined by factors including but not limited to the effective radius of the platform, the position angle of the structures on the platform with respect to the direction of rotation and the speed of rotation of the platform.

The capillary microvalves of the invention is based on the use of rotationally-induced fluid pressure to overcome capillary forces. Fluids which completely or partially wet the material of the microchannels (or reservoirs, reaction chambers, detection chambers, etc.) which contain them experience a resistance to flow when moving from a microchannel of narrow cross-section to one of larger cross-section, while those fluids which do not wet these materials resist flowing from microchannels (or reservoirs, reaction chambers, detection chambers, etc.) of large cross-section to those with smaller cross-section. This capillary pressure varies inversely with the sizes of the two microchannels (or reservoirs, reaction chambers, detection chambers, etc., or combinations thereof), the surface tension of the fluid, and the contact angle of the fluid on the material of the microchannels (or reservoirs, reaction chambers, detection chambers, etc.) . Generally, the details of the cross-sectional shape are not important, but the dependence on cross-sectional dimension results in microchannels of dimension less than 500 $\mu$m exhibit significant capillary pressure. By varying the intersection shapes, materials and cross-sectional areas of the components of the microsystems platform of the invention, "valve" are fashioned that require the application of a particular pressure on the fluid to induce fluid flow. This pressure is applied in the disks of the invention by rotation of the disk (which has been shown above to vary with the square of the rotational frequency, with the radial position and with the extent of the fluid in the radial direction). By varying capillary valve cross-sectional dimensions as well as the position and extent along the radial direction of the fluid handling components of the microsystem platforms of the invention, capillary valves are formed to release fluid flow in a rotation-dependent manner, using rotation rates of from 100 rpm to several thousand rpm. This arrangement allows complex, multistep fluid processes to be carried out using a pre-determined, monotonic increase in rotational rate.

The instant invention provides arrangements on the microsystems platforms of the invention to provide three types of capillary microvalving applications. The invention provides capillary metering of precise amounts of a volume of a fluid sample from the application of a less precise volume of a fluid sample at an entry port on the microsystem platform. These embodiments of the invention provide for delivery of precise amounts of a sample such as a biological fluid sample without requiring a high degree of precision or accuracy by the operator or end-user in applying the fluid to the platform, and is advantageous in embodiments of the microsystems platforms of the invention that are used by consumers and other relatively unsophisticated users. The invention also provides laminar flow-dependent replacement of a fluid in a first chamber by a second displacement fluid in a second chamber on the platform. These embodiments of the invention provide approximately complete replacement of a fluid in one chamber on the platform with fluid from another, and thereby provide means for practicing sequential chemical reactions and other sequential processes on the platform under conditions wherein mixing of the two fluids is disadvantageous. The invention also provides platforms comprising microchannel junctions with fluid chambers and reservoirs wherein fluid transfer through the microchannel and into the fluid chamber is effected in a dropwise manner, whereby the fluid in a microchannel is transferred into the fluid chamber as a stream of droplets. These embodiments of the invention provide means for enriching a suspension or mixture of a particulate material in a solution, by providing enriched droplets containing a higher density of the particulate than in the original suspension or mixture, when subjected to centripetal acceleration. Advantageous particulate material include cells, for example.

In embodiments of the invention providing laminar flow of fluids, one fluid replaces another without appreciable mixing of the two fluids. Flow is laminar if the Reynolds number, R, is less than 2200, wherein the Reynolds number is calculated by the equation:

$$R = \rho u a / \mu$$

wherein $\rho$ is the density of the fluid, $\mu$ is the viscosity of the fluid, u is the mean fluid velocity and a is a characteristic dimension (such as the cross-sectional diameter of a circular channel). For aqueous solutions, where $\rho$ is 1 g/cm$^3$, $\mu$ is 0.01 dyne-sec/cm, the mean fluid velocity must be greater than 220 cm/sec for a chamber having a cross-sectional dimension of 1 mm. Typically, the mean fluid velocity is less than 10 cm/sec, so that the flow of fluid in the chambers of the rotors and platforms of the invention will be laminar.

A. Theoretical

All fluids can be characterized by interactions with solid substrates and gasses. These interactions are further characterized by interfacial tension, or the energy per unit area at the interface of the fluid with another substance. One result of interfacial tension is capillary action (see Adamson, 1976, *Physical Chemistry of Surfaces*, 3d ed., Wiley & Sons: New York). Under "wetting" conditions, the liquid and solid experience mutual attraction. In such cases, liquids may flow from a large reservoir into a smaller, more narrow tube, in order to maximize the area of the solid/liquid interface. Flow through the tube is inhibited if the tube opens to a sufficiently large diameter that the area of solid/liquid contact would decrease by additional flow. Conversely, under non-wetting conditions, liquids resist flow through a small diameter tube (see Gerhart & Ross, 1985, *Fundamentals of Fluid Mechanics*, Addison Wesley Publishing: Reading, Mass.). Flow can be initiated into a non-wettable tube by applying pressure to the fluid. If a fluid encounters a constriction in the tube, capillarity requires even the greater pressure to be applied. The above considerations relating the use of capillarity to manipulate fluid flow are elaborated in the discussion below.

Physical surface features of fluid containing solids are known to affect the behavior of fluids (see Columbus & Palmer, 1987, *Clinical Chemistry* 33; 1531). By the proper design of surface features and selection of materials, structures can be designed to allow fluid flow only when sufficient pressure is applied to the liquid. This force can be supplied using pumping means, gravity, or preferably, centripetal force due to rotation of microfabricated structures on centrifugal rotors and microplatforms provided as described herein and in International Patent Application, Publication No. WO97/21090.

The invention disclosed herein includes microvalve structures that allow:

starting and stopping liquid flow;

precise metering of liquid flow; and fluid partitioning, whereby particulates are concentrated prior to release.

Variables that affect the performance of these microvalve structures include:

size and shape of fluid reservoirs, channels and orifices;

hydraulic pressure exerted on the fluid (in centripetal embodiments, pressure is determined by platform radius and rotation rate); and fluid surface tension and interfacial energy of the interface between the fluid and the materials of the fluid flow system.

B. Illustrative Examples a. Capillary Forces

In general, capillary forces are understood to arise due to the effects of interfacial energy, i.e., the energy if interactions between materials, particularly fluids and especially liquid materials, at their interface with other materials (usually solids). For example, the interfacial energy per unit area the interface between a liquid material and its vapor is termed the surface tension of the liquid ($\gamma$). One manifestation of surface tension is observed at a curved liquid-vapor interface. There exists across such and interface a pressure drop $\Delta P$ wherein $$\Delta P = \text{Force/Area} = \gamma(1/R_1 + 1/R_2) \qquad (1)$$

where $R_1$ and $R_2$ are the principal radii of the curvature of the interface. These radii are defined by the spheres which would be tangent to the surface at any point. The sphere having the smallest radius tangent to the surface at such point had the first radius of curvature, $R_1$. The sphere having the largest radius tangent to the surface at such point had the second radius of curvature, $R_2$.

An example is a liquid-vapor interface which is locally spherical; the radii of curvature are then equal to each other and to a sphere of radius r, and Equation 1 yields a pressure drop $$\Delta P = 2\gamma/r \qquad (2)$$

from the liquid side of the interface to the vapor side. This is illustrated in cross-section in FIG. 1a. The physical implication is that such a surface would expand into the vapor, increasing the radii of curvature and decreasing the pressure drop. It will be recognized that a saddle-shaped surface (where the radii of curvature arc equal in magnitude but opposite in sign) has no pressure drop, as shown by application of Equation 1.

Figure 1B:
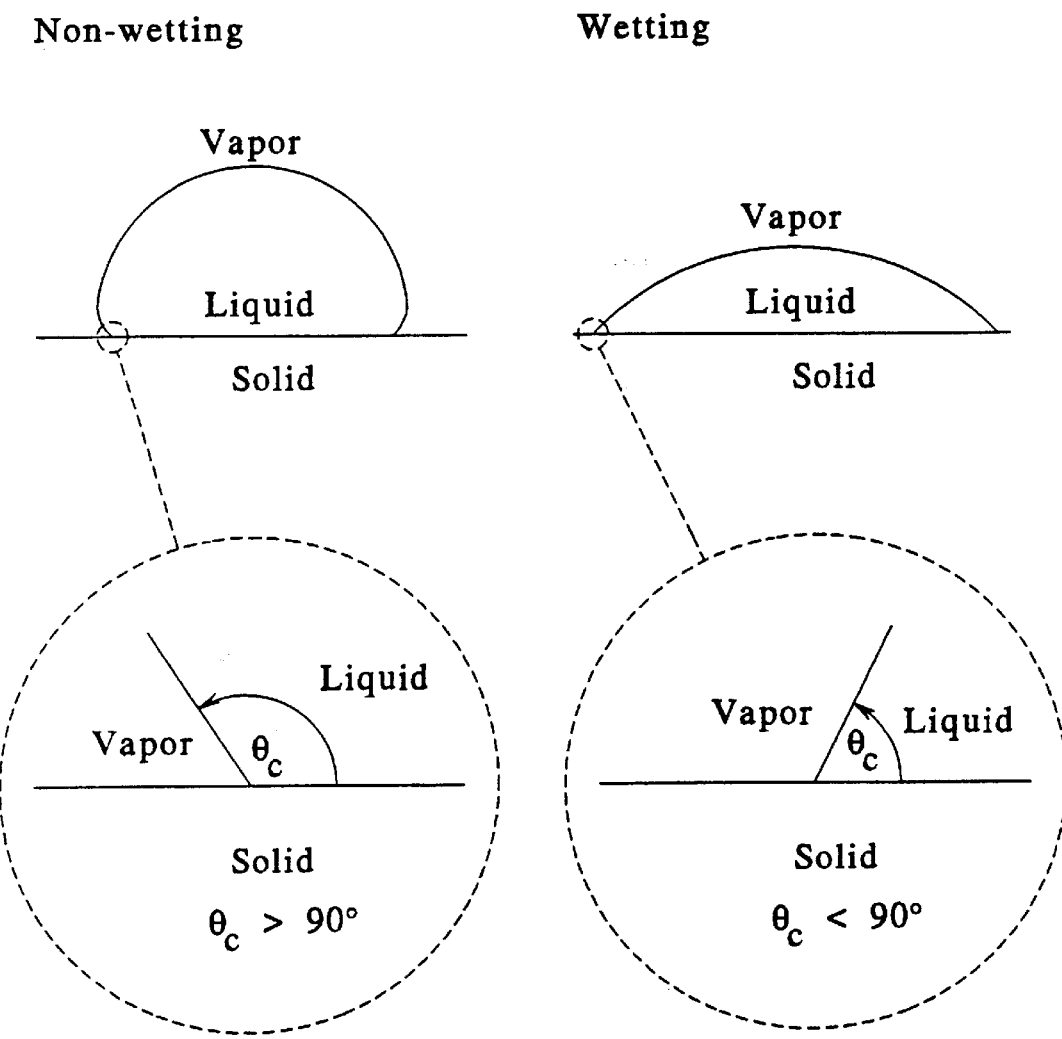
FIG. 1b shows the contact angles and behavior of fluids on wetting and non-wetting surfaces.

Another interface of interest is that between a liquid and a solid. The energy difference between the liquid-solid interface and the liquid-vapor interface can be expressed by an equation involving the surface tension of the liquid, $\gamma$, and the contact angle, $\Theta_c$, of the contact line where the liquid-solid, liquid-vapor and solid-vapor interfaces meet. This relationship is shown in FIG. 1b, where the relationships between these interfaces are illustrated for a non-wetting )left side of the Figure) and wetting (right side of the Figure) interaction between solid and liquid are illustrated. The behavior of the liquid in either case is determined by the equation:

$$\gamma_{sv} - \gamma_{ls} = \gamma \cos \Theta_c \qquad (3)$$

where $\gamma_{sv}$ is the energy per unit area of the solid-vapor interface, $\gamma_{ls}$ is the energy per unit area of the liquid-solid interface, and $\gamma$ is the energy of the liquid-vapor interface (equal to the liquid surface tension). For contact angles $\Theta_c$ greater than 90°, the liquid does not wet the solid, and "beads" on the solid surface. For contact angles $\Theta_c$ less than 90°, the liquid wets the solid, and spreads onto the solid surface. This behavior is illustrated in the Figure, where the contact angle formed between the liquid, solid and vapor is shown in exaggerated detail for each alternative contact angle.

In the present invention, Equation (1), which describes the pressure drop supported across a liquid-vapor interface, and Equation (3), which expresses differences in interfacial energies, are employed to determine the arrangement of surfaces comprising the microvalve structures and contours and change in the surface area of the solid structures that promote or inhibit fluid flow. These parameters are also used to provide fluid metering devices as described herein.

a. Capillarity at the Junction of Vessels With Different Cross-Sectional Areas

In the present invention, the contact angle is manipulated by the choice of the arrangement of the surfaces comprising the microvalve structures and combined with changes in surface area of the solid structures to either promote or inhibit fluid flow. Fluid flow can be "active" (i.e., promoted by the application of pressure or centripetal force), or "passive" (i.e., promoted or inhibited solely by the capillary forces according to the principles discussed above). To illustrate these principles with clarity and simplicity, the capillary orifices and channels or tubes discussed herein comprise circular cross-sectional areas. It will be understood that the precise shape of the capillary orifice affects the applied pressures at which the microvalves of the invention permit fluid flow, and that the manner in which pressure is thus affected is the minimum interfacial energy of the fluid/surface and fluid/vapor interfaces at the junction between the channel, tube or orifice and the reservoir.

Figure 2A:
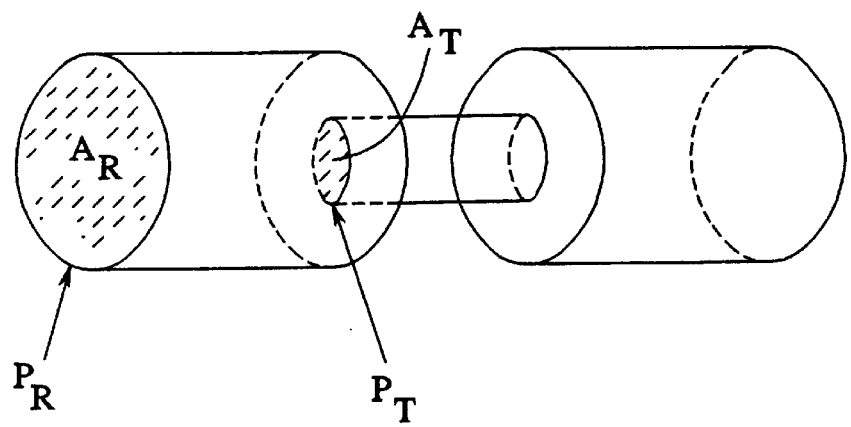
FIG. 2a is a schematic drawing of the dimensional and pressure relationships between capillaries and chambers of different cross-sectional dimensions.
Figure 2A:
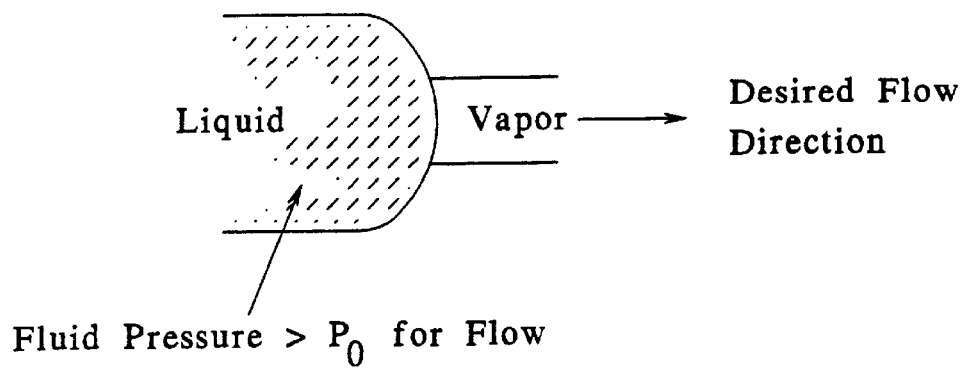
Figure 2B:
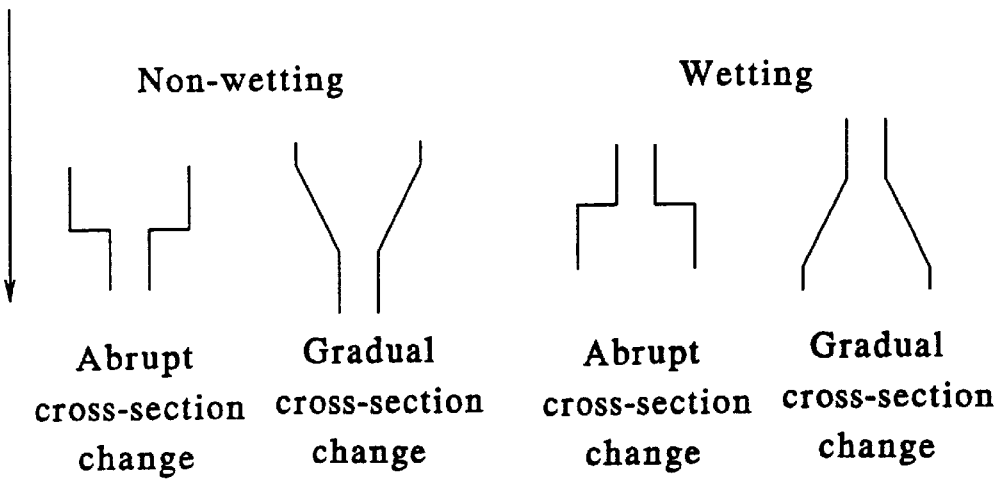
FIG. 2b illustrates capillary junction geometries for wetting and non-wetting surfaces.

One example of fluid flow as practiced by the microvalve structures of the invention is shown in FIGS. 2a and 2b. FIG. 2a shoes two reservoirs (R) having arbitrary cross-sectional area $A_R$ and cross-sectional perimeters PR connected by a tube (T) of smaller cross-sectional area $A_T$ and perimeter $P_T$, so that $P_R/A_R < P_T/A_T$. (The tube is provided for illustration; the analysis and discussion provided herein are equally applicable to an orifice of the same cross-sectional area. Further, the reservoirs can be different, provided that the dimensions of the orifice are smaller that those of either reservoir.) A volume of fluid is introduced into one reservoir, and is free to partition between the reservoirs and the connecting tube as a result of capillary forces; air holes may be placed appropriately to remove air displaces by fluid flow. The capillary forces experienced by the liquid as it is introduced into the tube is expressed by a pressure, the magnitude of which is given by the following equation:

$$P_C = \text{Force/Area} = \gamma\{(-P_R/A_R)\cos\Theta_R + (P_T/A_T)\cos\Theta_T\} \qquad (4)$$

where $\Theta_R$ and $\Theta_T$ are the contact angles between the liquid and the surface of the reservoir and the tube, respectively. For circular reservoirs and channel, the contact angle provides a radius of curvature whose magnitude of curvature is smaller within the tube that within the reservoir, resulting in pressure differences between these two interfaces that leads to fluid flow.

The cross-sectional areas and perimeters of importance are those at the contact line(s) between solid, liquid and vapor. These parameters may be a function of the position of the interfaces of the reservoir(s) and tube(s); and example of this dependence of the contact angle on surface shape configuration include funnel-shaped tubes and spherical reservoirs. For most cross-sectional shapes, the ratio of $P_i/A_i$ varies as a inverse of the average cross-sectional diameter of the reservoir or tube. This means that the volume of the reservoir or tube of smaller average diameter makes the larger contribution to the pressure define in Equation (4) (e.g., the component of smaller average diameter in FIGS. 2a and 2b is a tube).

Because Equation (4) is the pressure that resists fluid flow in the direction of the tube (to the right in FIG. 2a), a pressure P* of greater magnitude and opposite direction must be applied across the interface at the tube entrance; this pressure can be applied to the fluid in the reservoir on the left of the Figure. The magnitude of such a pressure P* is given by the following equation:

$$P^* = \gamma \{(P_R/A_R) \cos \Theta_R - (P_T/A_T) \cos \Theta_T\} \tag{5}$$

If the applied pressure is greater than the opposing pressure arising from capillary forces, fluid will flow from the left reservoir into the tube. For a non-wetting fluid emerging from the orifice, the maximum resisting force occurs when the liquid-vapor interface points along the edges of the tube or orifice; hence, this is the resisting force or pressure that must be overcome:

$$P^* = \gamma \{(P_R/A_R) \cos \Theta_R + (P_T/A_T)\} \tag{6}$$

(where $P_R$ and $A_R$ refer to the left-hand reservoir in the Figure). In this arrangement, Equation (5) defines the pressure necessary to initiate fluid flow into the microvalve. Equation (6) defines the pressure that must be applied to cause flow into the right-hand reservoir.

If both contact angles are greater than or equal to 90°, the pressure at the interface is negative (i.e., points to the left in FIG. 2a). In order to force liquid from the reservoir into the tube, a pressure of at least the same magnitude must be applied on the fluid in the opposite direction (to the right in the Figure). If the pressure is greater than P* as given in Equation (6), the fluid will further flow from the tube into the second (right) reservoir. If the contact angles are less than 90°, the pressure at the interface is positive (i.e., it points to the right in FIG. 2a). In this case, fluid is drawn into the tube by capillary action, filling the tube until an interface is formed at the junction of the tube with the second large reservoir at the end of the tube (i.e., on the right in FIG. 2a). At this interface, the liquid assumes a configuration wherein there is no pressure difference across the left-hand and right-hand interfaces (given by Equation (1)) (i.e., the pressures are equal). To move fluid into the right-hand reservoir, a pressure must be applied as given by Equation (5).

The pressure necessary for flow into the second reservoir in the case of a wetting solution can be increased through the use of inlets into the second reservoir that are shaped conically (e.g., similar to the tip of macroscopic pipette). Alternatively, micron-sized textures as described in Columbus (Id.) can be used, or a combination thereof For conical-shaped inlets, Equation (6) gives the pressure necessary for flow, as described above in the case of a non-wetting solution, but with the radius of curvature determined by the outer radius of the conical surface.

In practice, wetting fluids emerging from capillaries are more susceptible to the effects of pressure fluctuation, vibrations and other such phenomenon, which can result in premature wetting of the exit area. This is because the wetting fluid is retained at the junction of the tube and a fluctuation driving fluid into the reservoir results in a smaller capillary force than was exerted when the fluid was at the junction. A non-wetting fluid is retained at the entry to a tube or channel; a fluctuation driving fluid into the tube results in the same capillary force as at the junction, and hence the fluid interface may be pushed back by capillary forces once the cause of the fluctuation has subsided.

One means for controlling pressures necessary for flow are provided by textures in the surface material, such as concentric rings around the exit port: such textures have increased resistance to flow along the surface relative to a smooth surface so that a fluid droplet may form with a 90° angle as described above in the case of a non-wetting solution. In this case, Equation (6) gives the minimum pressure necessary for flow.

Equations (4), (5) and (6) define microvalve principles and a construction method for making microvalves for controlling fluid flow in Microsystems and microplatforms. Succinctly, channels of varying cross-sectional area are used in combination with applied pressures to "valve" fluids through certain control points in the microplatform or other microsystem. A simple example of such a microvalving arrangement is a succession of chamber connected by tubes or channels so that initiation of flow in each tube is achieved by stepwise increases in applied pressures. Non-limiting examples of shapes of "valving" orifices useful in the microvalves of the invention are illustrated in FIG. 2b.

b. Capillary Forces and the Creation of Droplets at a Tube Orifice

Figure 3A:
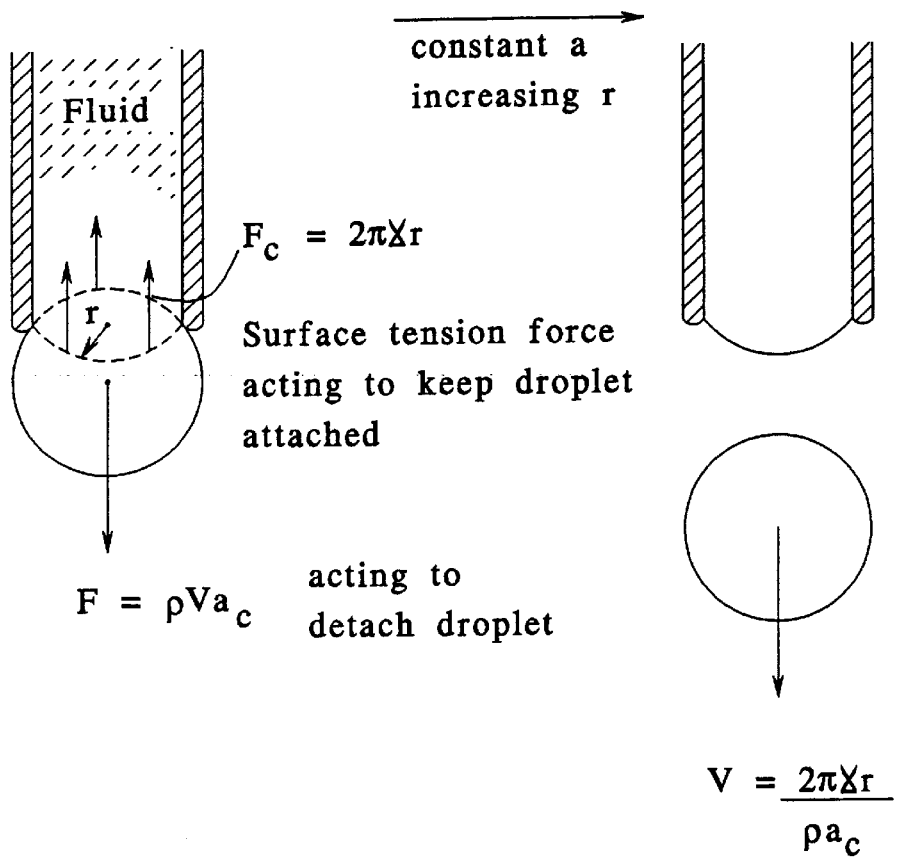
FIGS. 3a and 3b illustrate geometries for droplet formation from a capillary.
Figure 3B:
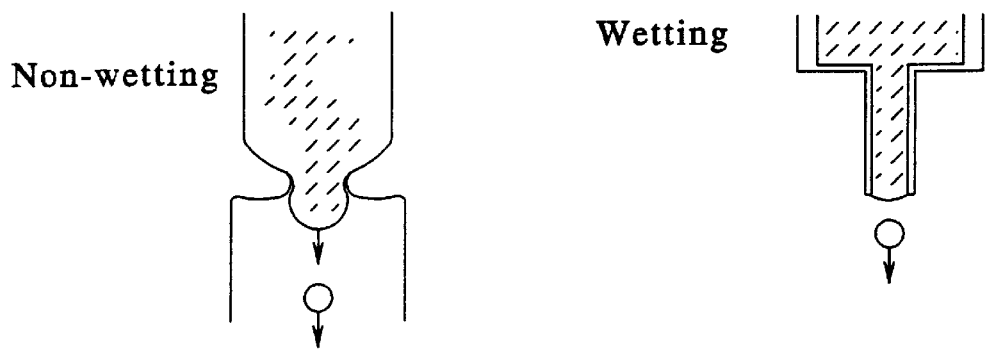

Another aspect of the disclosed invention is the dropwise release of fluid from a channel, tube or simple orifice between reservoirs or chambers. A droplet of a fluid will detach from the end of a tube containing the fluid when the force on the droplet (in a direction away from the tube or orifice) is greater that the force of the surface tension holding the droplet on the he tube (discussed more fully in Adamson, ibid.). This relationship is described by the following equations:

$$F = \rho V a_c = k(2\pi r \gamma) \tag{7a}$$

or, solving for the volume V of the droplet $$V = k(2\pi r \gamma)/\rho a_c \tag{7b}$$

wherein $a_c$ is the acceleration which the free droplet would experience due to the applied force ( e.g., pressured or gravity); V is the volume of the detached droplet; $\rho$ is the liquid density; r is the approximate radius of the tube from which the drop "falls" (defined as the inner radius for a non-wetting surface, and the outer radius of a tube tip for a wetting surface); and k is a geometry-dependent coefficient related to $\gamma/V^{1/3}$ ranging in magnitude from 0.5 to 1. The value of k appropriate for the conditions under consideration is determined self-consistently between values of k which are tabulated as a function of different values of $\gamma/V^{1/3}$. This requires an iterative approach. An initial "guess" for the value of k is made, and then Equation (7b) is used to calculate V. This value of V is then used to look up an appropriate value for k in the aforesaid Table. If the value of k determined from the Table is different from the original assumption, the correct value must lie therebetween, and an internmediate approximation is made and the analytical process repeated. This process is continued until a value of k is determined that is consistent with the calculated value as described above. For example, a choice of k is determined that is consistent with the calculated value as described above. For example, a choice of k=0.75 might lead to value of $\gamma/V^{1/3}=0.1$, which tabulated values of k indicate are appropriate for k=0.95. The value of k is then adjusted and the calculation repeated iteratively until the actual value of k for a given instance is determined. The other symbols have the meanings and values described above in previous equations. Release of a droplet from the end of a tube is illustrated in FIGS. 3a and 3b. FIG. 3a shows the release of a droplet under the influence of a force (such as pressure or gravity); the droplet is shown to be released when a sufficient volume is achieved in response to the applied force; release occurs when the surface tension holding the droplet is insufficient to counter the force pulling the droplet away from the end of the tube. It is recognized that the shape of the orifice determines to a degree the volume of the detached droplet for a given tube cross-sectional area and applied acceleration (pressure), and that droplet formation and the magnitude of the requisite pressure also depends on whether the surface is wetting or no-wetting. FIG. 3b shows orifice shapes that facilitate droplet formation for both wetting and non-wetting.

c. Use of Centripetal Acceleration to Apply Pressure to a Liquid

Figure 4:
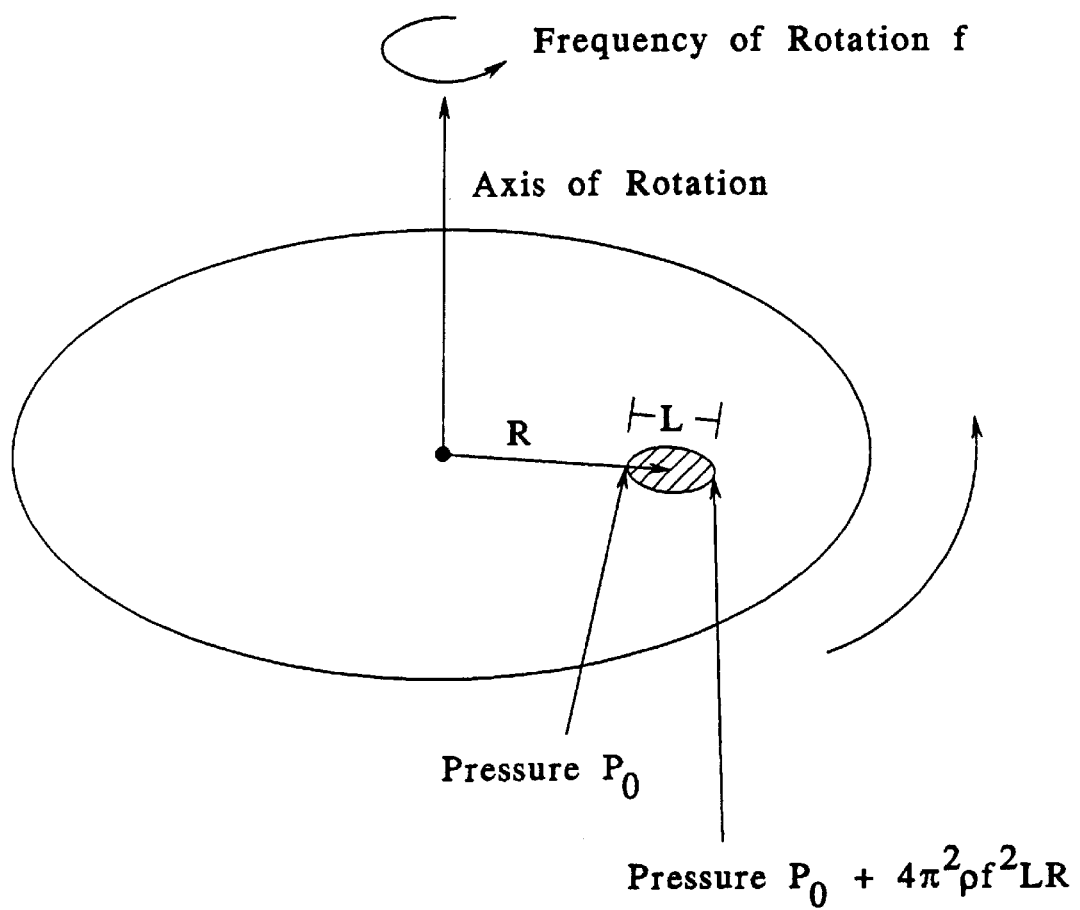
FIG. 4 is a schematic of the pressure relationships in a chamber on a rotating platform of the invention.

One means for providing a applied force to motivate fluid flow is the application of a centripetal force; this means is particularly important on centrifugal rotors and in microplatform systems as disclosed in International Application WO97/21090. In microplatform arrangements, a reservoir and connecting channels are arrayed on a microplatform, preferably a circular shaped disk, at a radial distance R from the center of rotation. Such an arrangement is shown if FIG. 4, wherein the reservoir is characterized by the radial distance from the center of the disk (R), its extent along that radius (L) and the rotation rate f in revolutions per second. The pressure at the outer radius of the fluid due to centripetal acceleration is given by the following equation:

$$P = 4\pi^2 f^2 \rho LR \tag{8}$$

where $\rho$ is the fluid density. It can be seen that the pressure at the outer extent of the reservoir will differ from the pressure at the inner extent of the reservoir by $4\pi^2 f^2 \rho LR$.

The driving force for fluid motion or creating fluid pressures is the force on matter which results from centripetal acceleration. A device may rotate at an angular rate of f in revolutions/sec and angular frequency $$\omega = 2\pi f \tag{9}$$

The centripetal acceleration (or acceleration oriented along the radius at a radial distance R from the center of the uniformly-rotating disk) is $$\alpha_c = \omega^2 R \tag{10}$$

A mass m in such uniform circular motion is subject to a centripetal force $$F_c = m\alpha_c = m\omega^2 R \tag{11}$$

which is directed inward along the radius to the center of rotation. If the mass is held fixed at this radius, the device causing rotation supplies this force; this is the origin of the static pressure in liquid columns discussed below. If the mass is placed on top of a trap-door above a radially-oriented tube, and the trap-door opened, the inertia of the mass will cause it to accelerate down the tube; this is the basis for driving fluids radially outward on a rotating disk.

Rotation may create a static pressure in a non-flowing fluid. Assume a column of liquid extending from an inner radius $R_0$. The tube may be along the radius or inclined at an angle to the radius. Let the pressure at position $R_0$ be defined as $P_0$, which is for example atmospheric pressure. The excess pressure due to rotation of the liquid at Position R such that $R_0 < R$ is found by integrating the centripetal force per unit area for liquid of density p from position $R_0$ to R:

$$P - P_0 = \int \rho \alpha_c = \rho \omega^2 / 2 \times (R^2 - R_0^2) \tag{12}$$

If the tube is filled, extending from the center, then this pressure is $$P - P_0 = (2.834 \times 10^{-4}) p f^2 R^2 \tag{13}$$

in pounds per square inch (psi) where R=radial position in cm, $\rho$=density in gm/cm$^3$, and f=frequency in revolutions/sec. Thus, the pressure (or the amount of centripetal force on a fluid) varies directly with the density of the fluid, and as the square of the radial position from the center of rotation as well as the square of the frequency of rotation.

To determine the velocity of liquid in motion in channels on a rotating disk, the equation of motion for the fluid must be solved. An element of fluid of radius a and length dR filling the circular channel has a mass dm subject to acceleration:

$$dm = \pi \rho \alpha^2 dR \tag{14}$$

The equation of motion for this fluid element is force= (mass) X (acceleration). The forces are centripetal forces, capillary forces due to differences in interfacial energies between the fluid and vapor and fluid and solid surfaces, and dissipative forces due to the viscosity of the liquid and nonuniformity of flow. Capillary forces are ignored; it is understood that centripetal force and/or external pressure may need to be applied to force liquid into channels which are not wetted. As an over-estimate of these dissipative forces, both the force for fully-developed laminar flow of a Newtonian fluid ($F_L$) and that due to non-uniform flow ($F_D$) are included:

$$F = m\alpha$$

$$F_c + F_L + F_D = dm\alpha_R \tag{15}$$

$$F_c + F_L + F_D = (\rho \pi \alpha^2 dR)\alpha_R \tag{15}$$

where $a_R$ is the acceleration of the fluid mass element along the radius and $$F_c = (\rho \pi \alpha^2 dR)\omega^2 R$$

$$F_L = -(8\mu \pi \alpha^2 dR)u$$

$$F_D = -(2\rho \pi \alpha^2 dR)u^2 \tag{16}$$

where $\mu$ is the viscosity and u is the radial velocity of the fluid. These last two expressions are standard-mechanics expressions for fully-developed and completely undeveloped laminar flow, such as at channel entrances/exits or at the ends of a flowing droplet. Also note that for tubes or channels inclined at an angle θ with respect to the radius $F_C$ would be replaced by ($F_C$) X cos θ. The final equation becomes $$(\rho \pi \alpha^2 dR)\omega^2 R - (8\mu \pi R)u - (2\rho \pi \alpha^2 u^2 dR) = (\rho \pi \alpha^2 dR)(du/dt) \tag{17}$$

where the radial acceleration of the fluid is defined by $\alpha_R - (du/dt)$. This is a differential equation for the fluid flow velocity.

This equation is solved for specific examples. Consider a droplet of fluid of length L moving in a radial channel of greater length than the droplet.

Because the fluid in the droplet all moves at the same velocity, dR may be replaced by L and R by the average position of the droplet, $\langle R \rangle = (R+L/2)$.
Dividing out common factors:

$$(\omega^2(R+L/2)/2)-(8\mu/\rho\alpha^2)u-2(u^2/L)=(du/dt) \quad (18)$$

This equation must be solved numerically. An approximation may be made which has been justified through comparison with numerical solutions. It consists of this: the negative terms on the left-hand-side almost entirely cancel the positive term. Then the right-hand-side can be set to 0 and a solution can be made to the resultant equation for the "terminal velocity" at position R, $u_0$ $$(\omega^2(R+L/2)/2)-(8\mu/\rho\alpha^2)u-2(u_0^2/L)=0 \quad (19)$$

This is a quadratic equation which has the solution $$u_0=-(B+\sqrt{B^2+4AC})/2A \quad (20)$$

with $$A=L/2$$
$$B=8\mu/\rho\alpha^2 \quad (21)$$
$$C=(\omega^2)(R+L/2)/2$$

In conventional units these become $A=2/L$, $B=320\mu/\rho D^2$ and $C=(19.74)f(2R+L)$ with $u_0$=fluid velocity in cm/sec; L=droplet length in cm; $\mu$=viscosity in poise; $\rho$=fluid density in gm/cm$^3$; D=2a=tube diameter in cm; and R=radial position of the fluid droplet in cm. As described, this expression gives the approximate velocity of a droplet of fluid in a tubular channel, the volume of the droplet resulting in droplet length being shorter than the channel length. This estimate assumes both viscous and non-viscous losses. The velocity of a fluid droplet will increase with increasing density and droplet volume (length), and decrease with increased viscosity. The velocity will increase with increased channel diameter, rotational velocity, and radial position.

Fluid flow velocity in a filled channel connecting a full chamber at position Ro and receiving reservoir at position $R_1$ is calculated by defining L in equation (19) and subsequent equations as the channel length, $L=R_1-R_0$. Then equation (21) with the definitions following equation (21) are used to calculate the flow velocity in the filled chamber as a function of radius.

The rate of fluid-flow is the product of velocity and channel area:

$$Q=u_0\pi\alpha^2=u_0\pi D^2/4 \quad (22)$$

where Q=flow in mL/sec; $u_0$=velocity in cm/sec (calculated from equations 20 and 21); and D=tube diameter in cm.

The time required to transfer a volume V from a reservoir to a receptacle through a tube or channel of length L depends on whether V is such that the tube is filled (length of a "droplet" of volume V in the tube would be longer than the tube itself) or unfilled by volume V. In the former case, this time is approximately the volume V of the fluid divided by the rate of flow Q; in the latter case it is approximately this calculated time multiplied by the ratio of the tube length to the resultant droplet length:

$$Dt=V/Q \text{ if } L \leq (4V/\pi D^2)$$
$$Dt=(V/Q)\times(4\pi D^2 L/4V), \text{ if } L>(4V/\pi D^2) \quad (23)$$

wherein Dt is the same time in seconds for fluid of volume V in mL flowing at rate Q in mL/sec to flow from a filled reservoir to a receptacle through a tube of length L and diameter D in cm. The rate of flow Q is calculated from eq. (22) and by extension equations (20) and (21) and the definitions of the parameters following equation (21). The time Dt increases with increasing volume transferred and decreases with increasing flow-rate.

Fluid characteristics such as pressure and velocity are related to physical parameters of the disk, such as disk radius and speed of rotation, as described above. These relationships are illustrated in FIGS. 5A, 5B, 6A, 6B, 7A, 7B, and 8A through 8D, derived from the above equations for water at room temperature, with $p=1$ gm/cm$^3$ and $\mu=0.001$ poise. These figures delineate the most relevant parameters of fluid movement on a rotating disk.

Figure 5A:
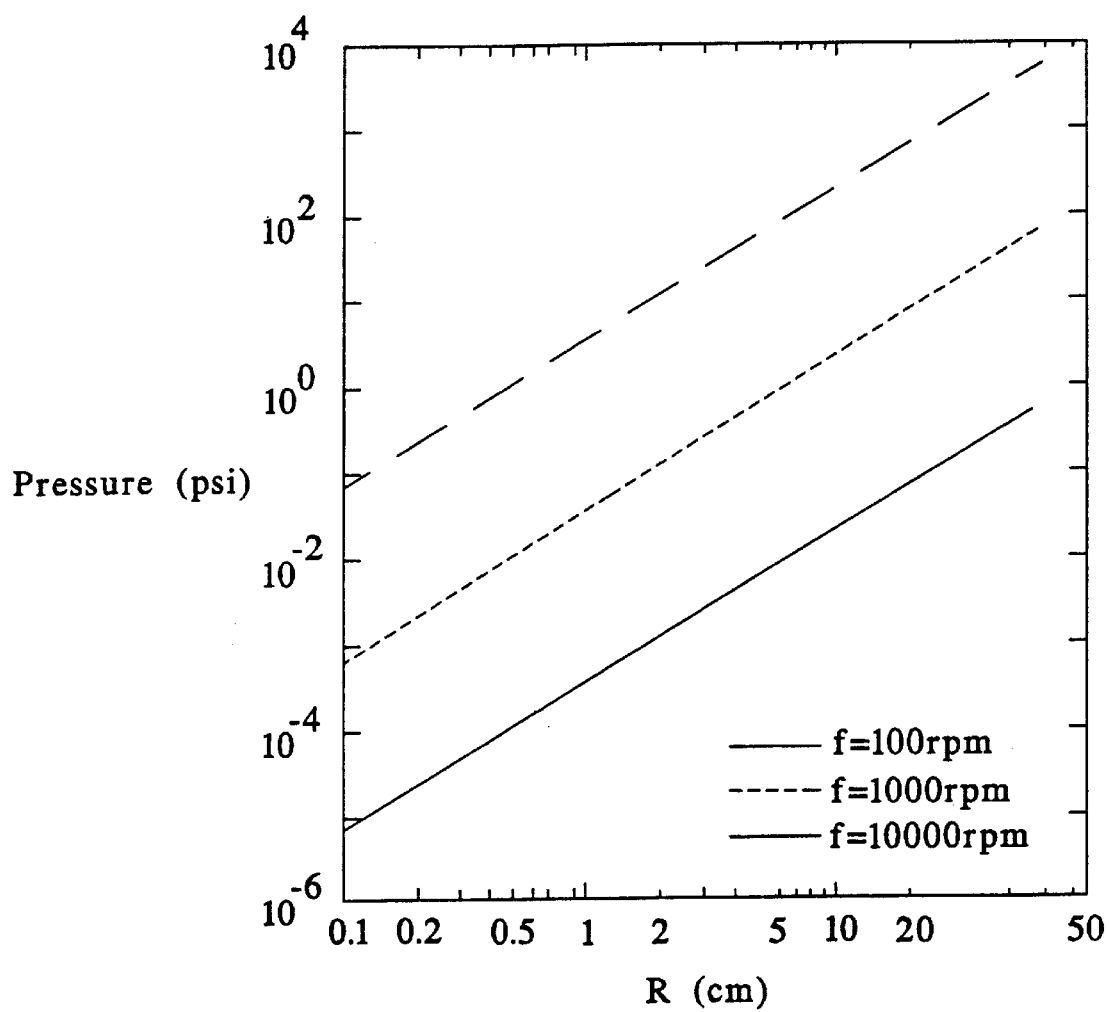
FIG. 5A is a graph.
Figure 5B:
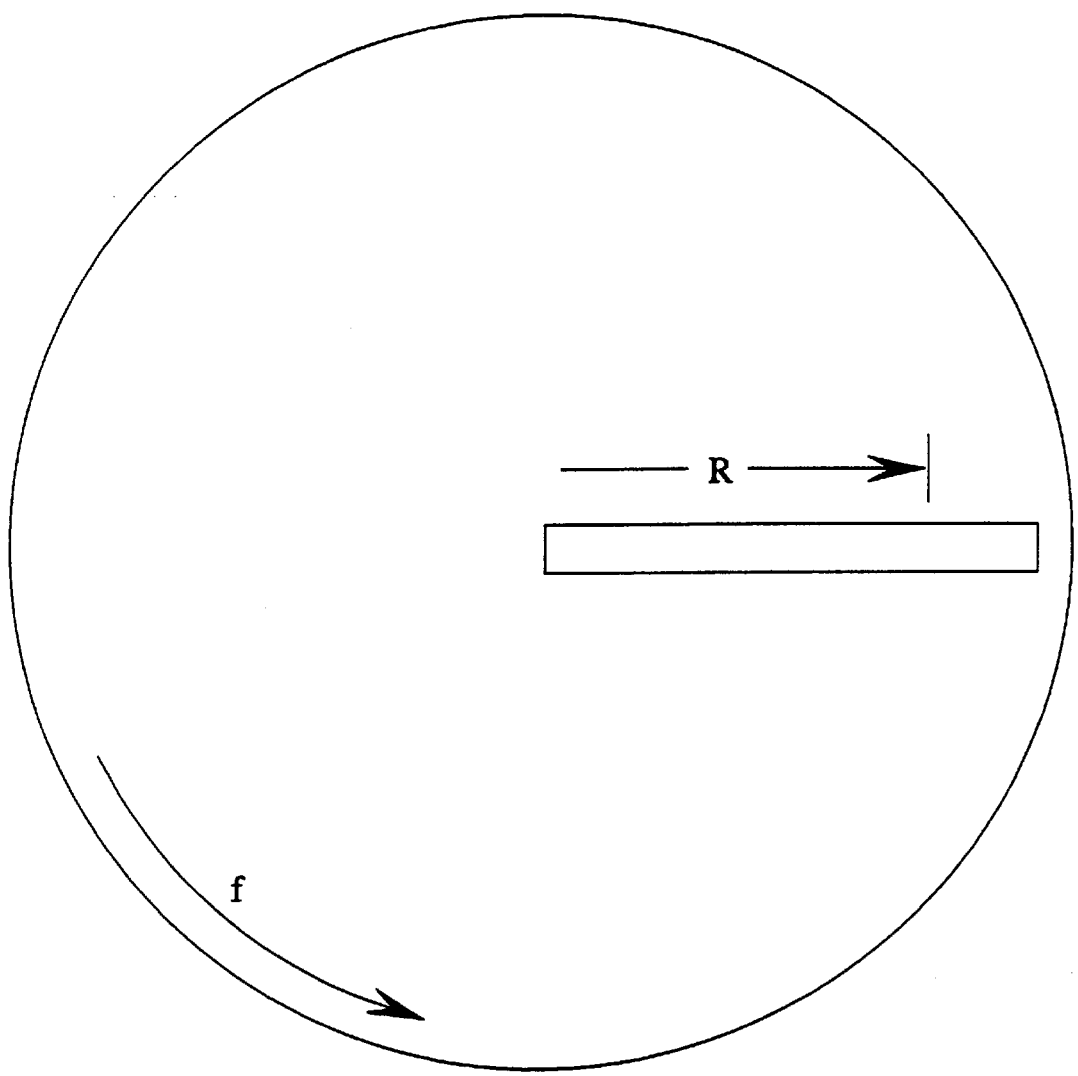
FIG. 5B is a schematic diagram of the arrangement of a channel on a disk of the invention as described with relation to Equation 13.

FIG. 5A illustrates the relationship between static pressure in a fluid-filled tube 30 cm in length as a function of radial distance (R) and rotation rate (f), calculated from Equation 13. The arrangement of the tube on a rotating disk is shown in FIG. 5B. It can be seen that pressures of between 0 and 10,000 psi can be generated in the tube at rotational speeds of 0 to 10,000 rpm. Pressures of this magnitude are conventionally used, for example, to drive high pressure liquid chromatography (HPLC).

Figure 6A:
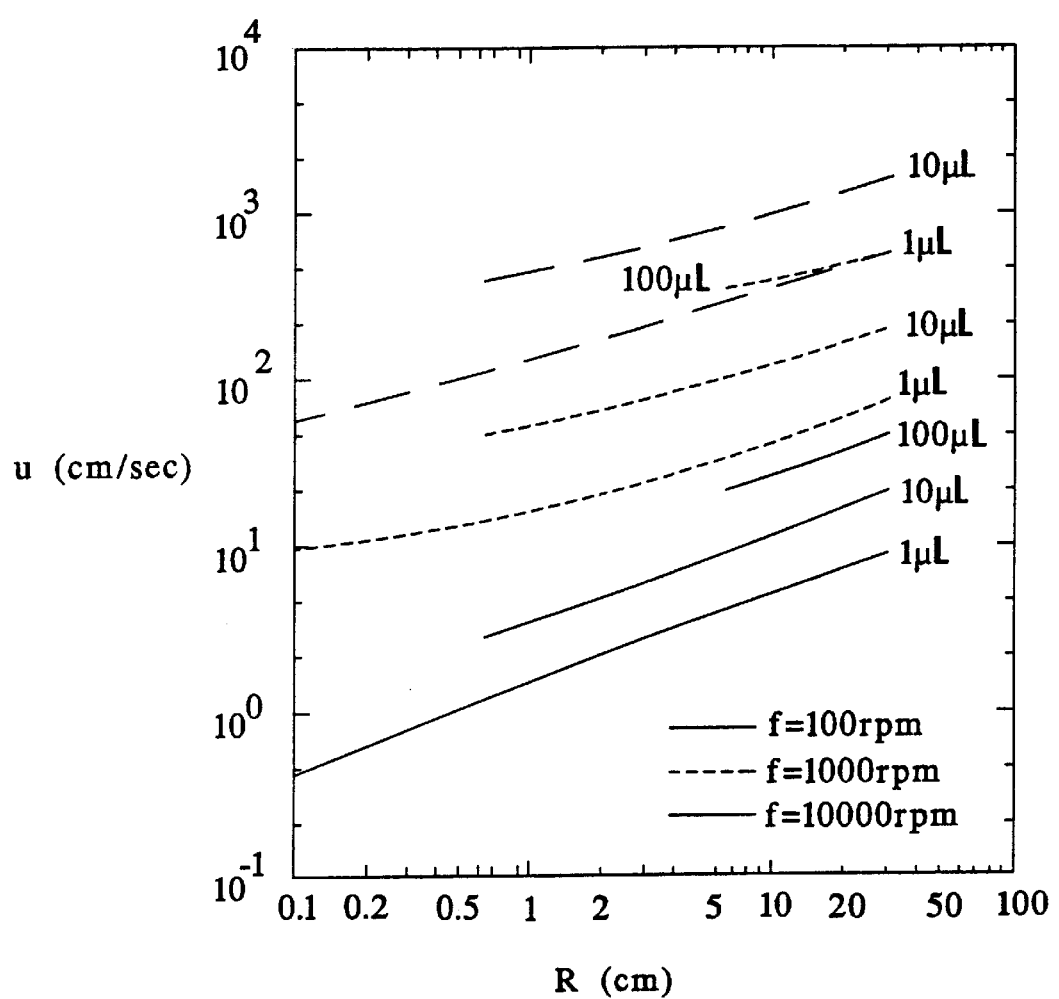
FIG. 6A is a graph.
Figure 6B:
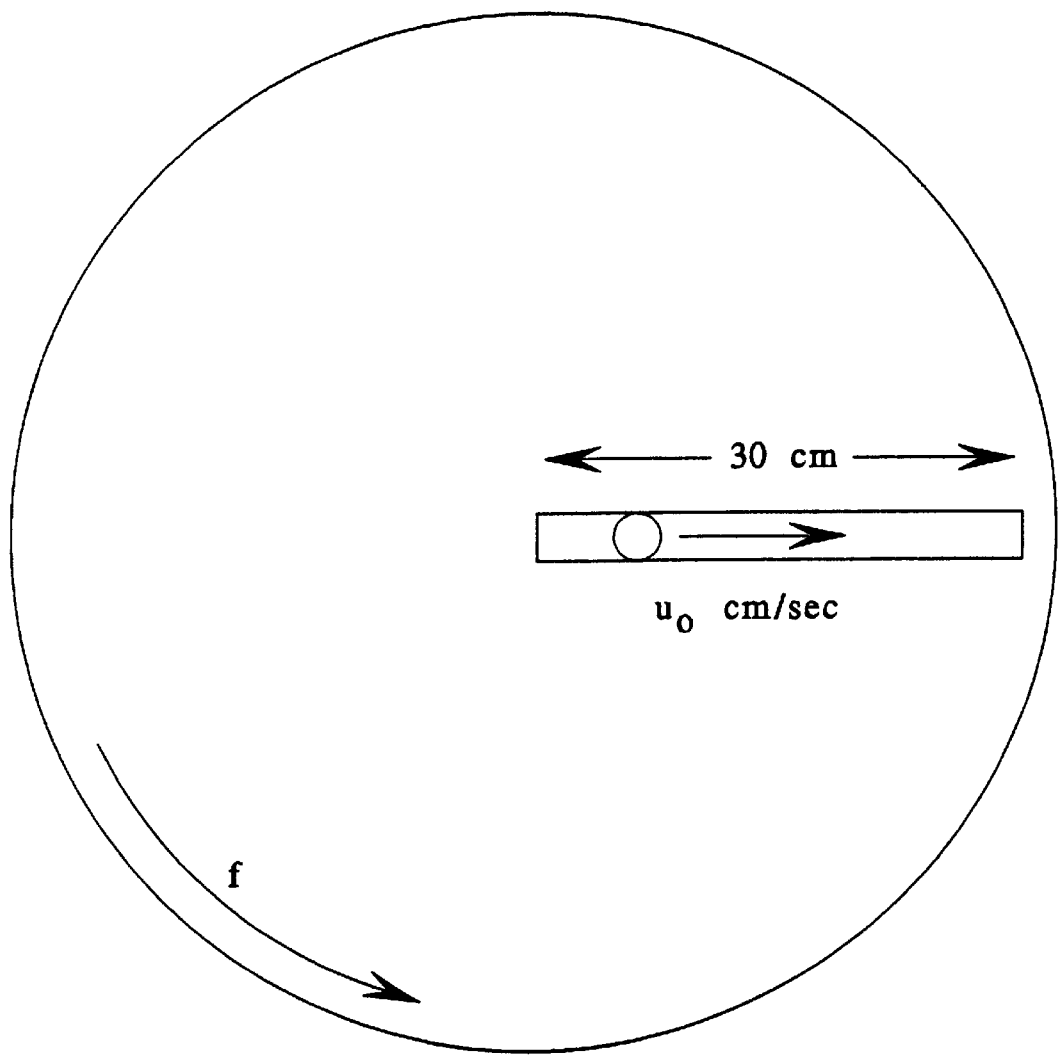
FIG. 6B is a schematic diagram of the arrangement of a channel on a disk of the invention as described with relation to Equations 20 and 21.

FIG. 6A shows the radial velocity of droplets having volume of 1, 10 and 100 $\mu$L droplets moving in an empty, 30 cm long tube with a diameter of 1 mm, calculated from Equations 20 and 21. The rube is aligned to extend along the radius of the disk from the center, and the disk is rotated at speeds of 100, 1,000 or 10,000 rpm. The arrangement of the tube on a rotating disk is shown in FIG. 6B. These velocities may be used to calculate the transfer time for fluid droplets. For example, a 1 $\mu$L droplet flows at approximately 20 cm/sec when at a position 2 cm from the center of a disk rotating at 1,000 rpm. Hence, the time to flow through a 1 cm tube can be calculated to be about 0.05 seconds. (For tubes oriented non-radially at an angle of 45° to the direction of rotation, the velocity drops by a factor of 30%.)

Figure 7A:
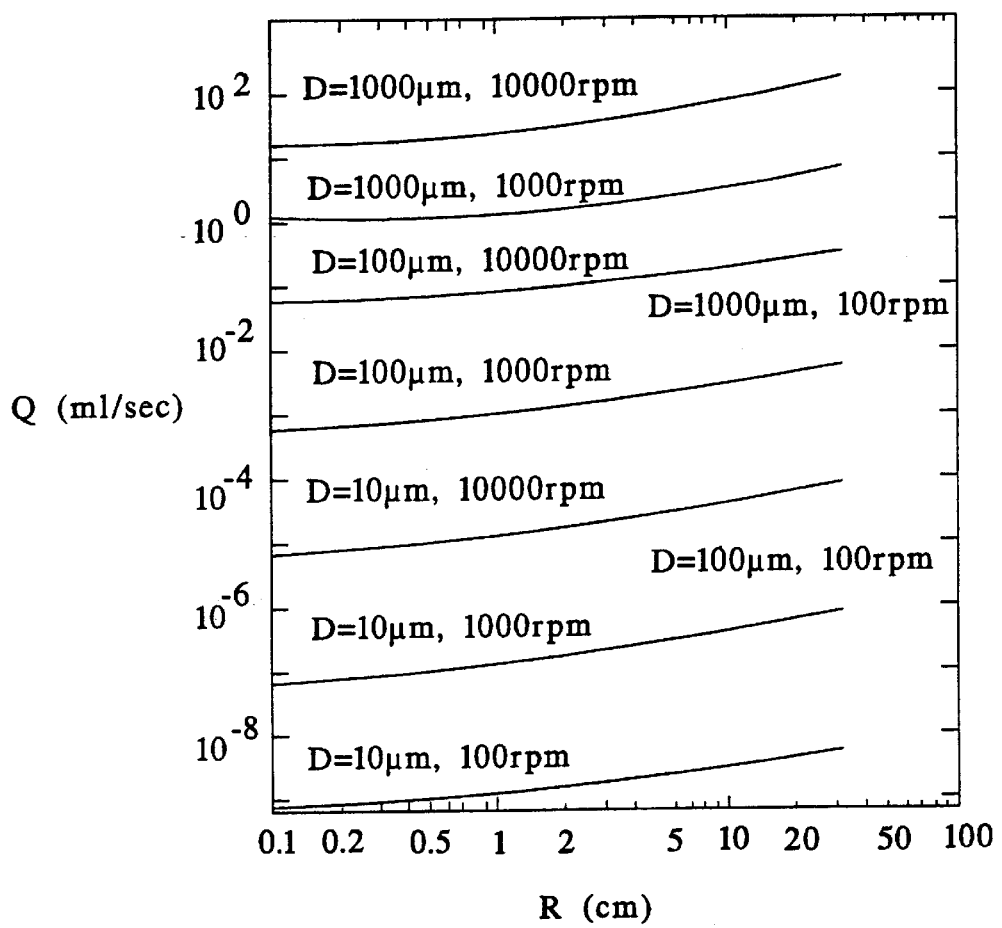
FIG. 7A is a graph.
Figure 7B:
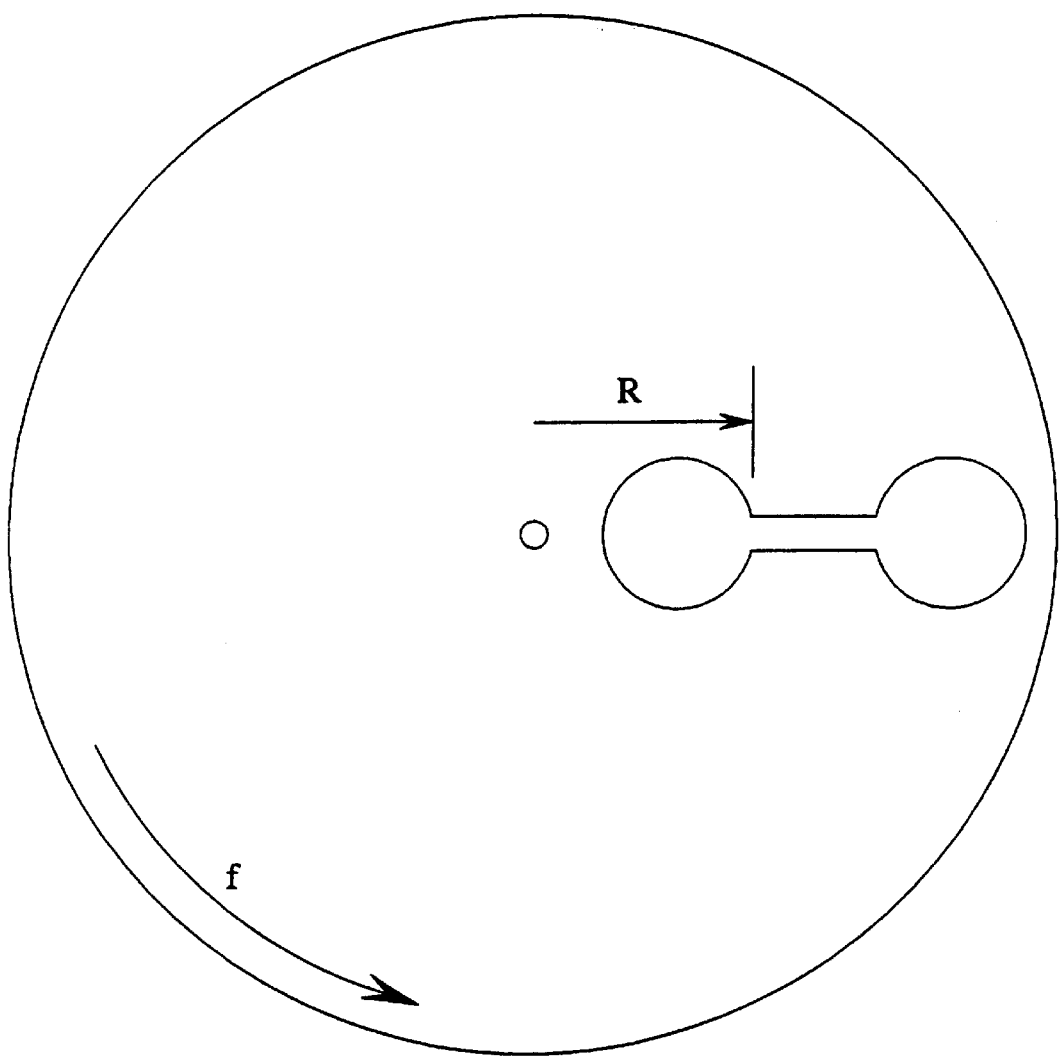
FIG. 7B is a schematic diagram of the arrangement of a channel on a disk of the invention as described with relation to Equation 22.

FIG. 7A illustrates flow rates in a 5 cm fluid-filled tube of different diameters. The tubes are each placed on a rotating disk and connects two radially oriented reservoirs, shown in FIG. 7B. According to Equation 22, flow rates are a function of radial position of the tube (which vary in this example from 2–30 cm), the tube diameter (10 $\mu$m, 100 $\mu$m, or 1,000 $\mu$m), and rotation frequency (100, 1,000 or 10,000 rpm). (As above, for tubes with a non-radial orientation of 45°, the velocity drops by a factor of 30%). Droplet velocities shown in FIG. 7A were calculated by Equation 11 and flow rates determined using Equation 12.

Figure 8A:
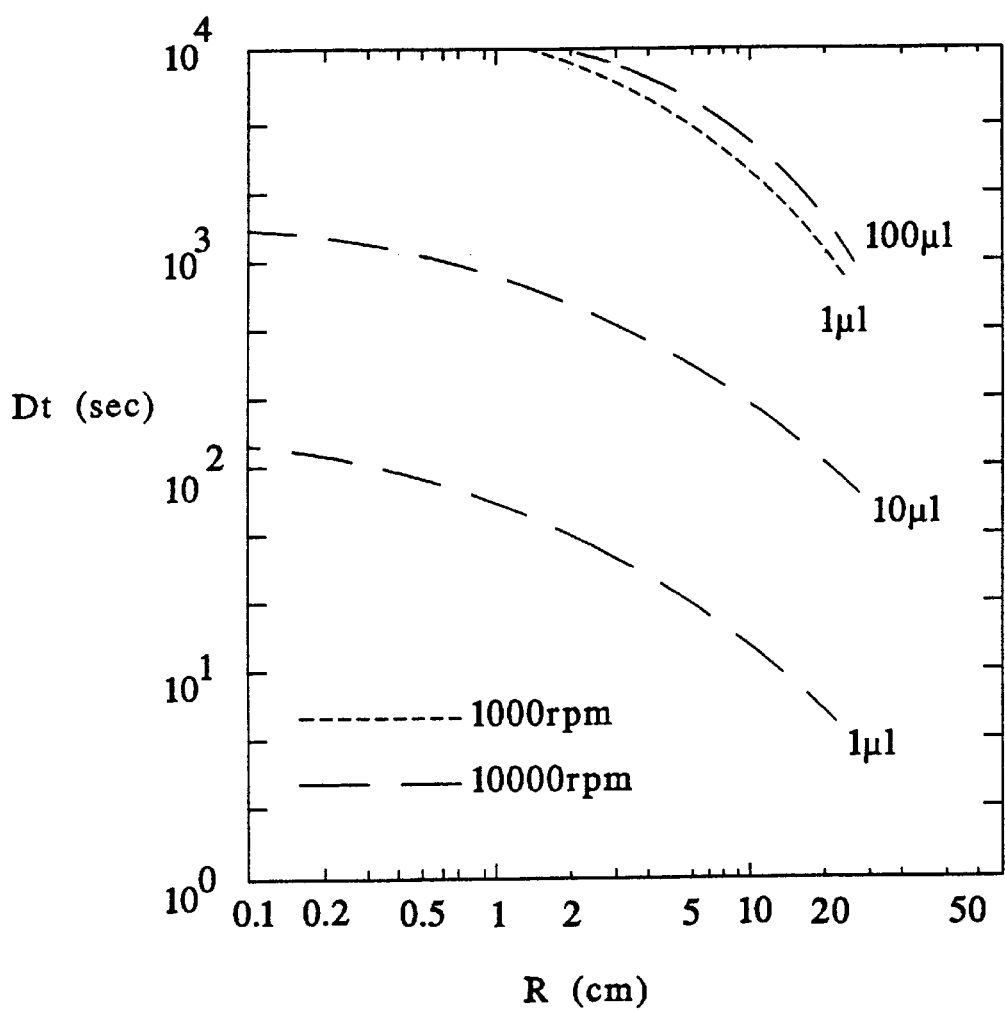
FIGS. 8A, 8B and 8C are graphs.
Figure 8B:
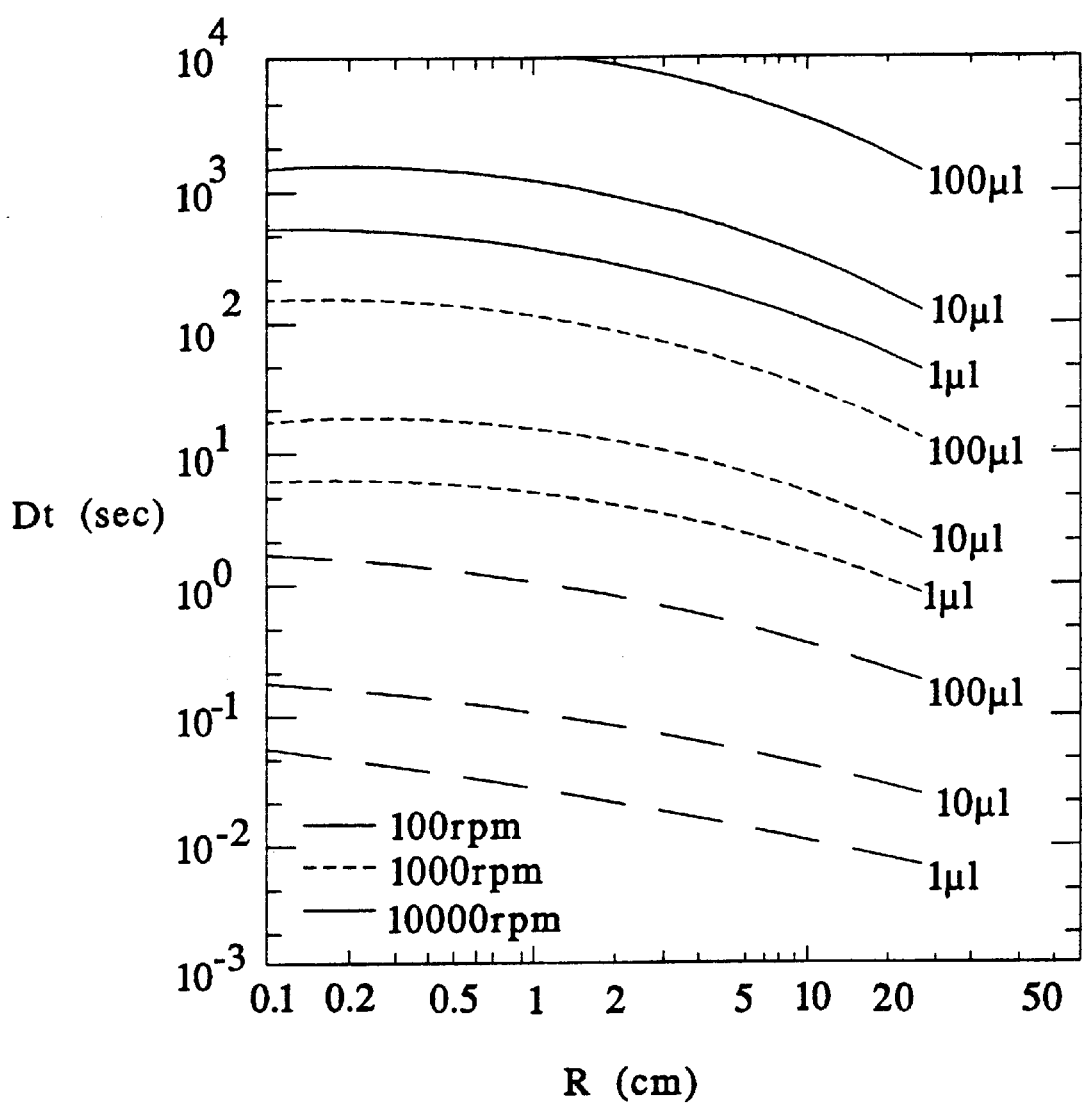
Figure 8C:
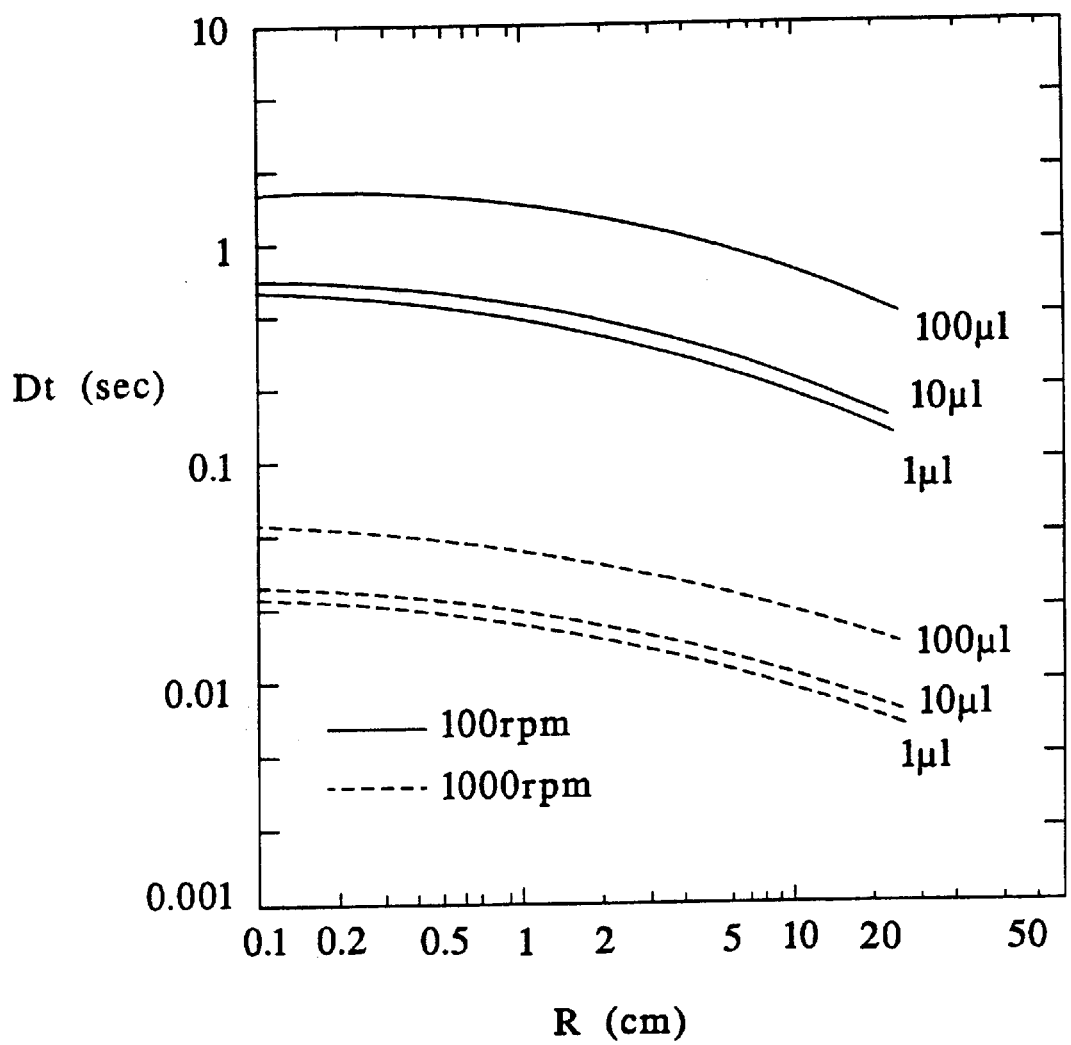
Figure 8D:
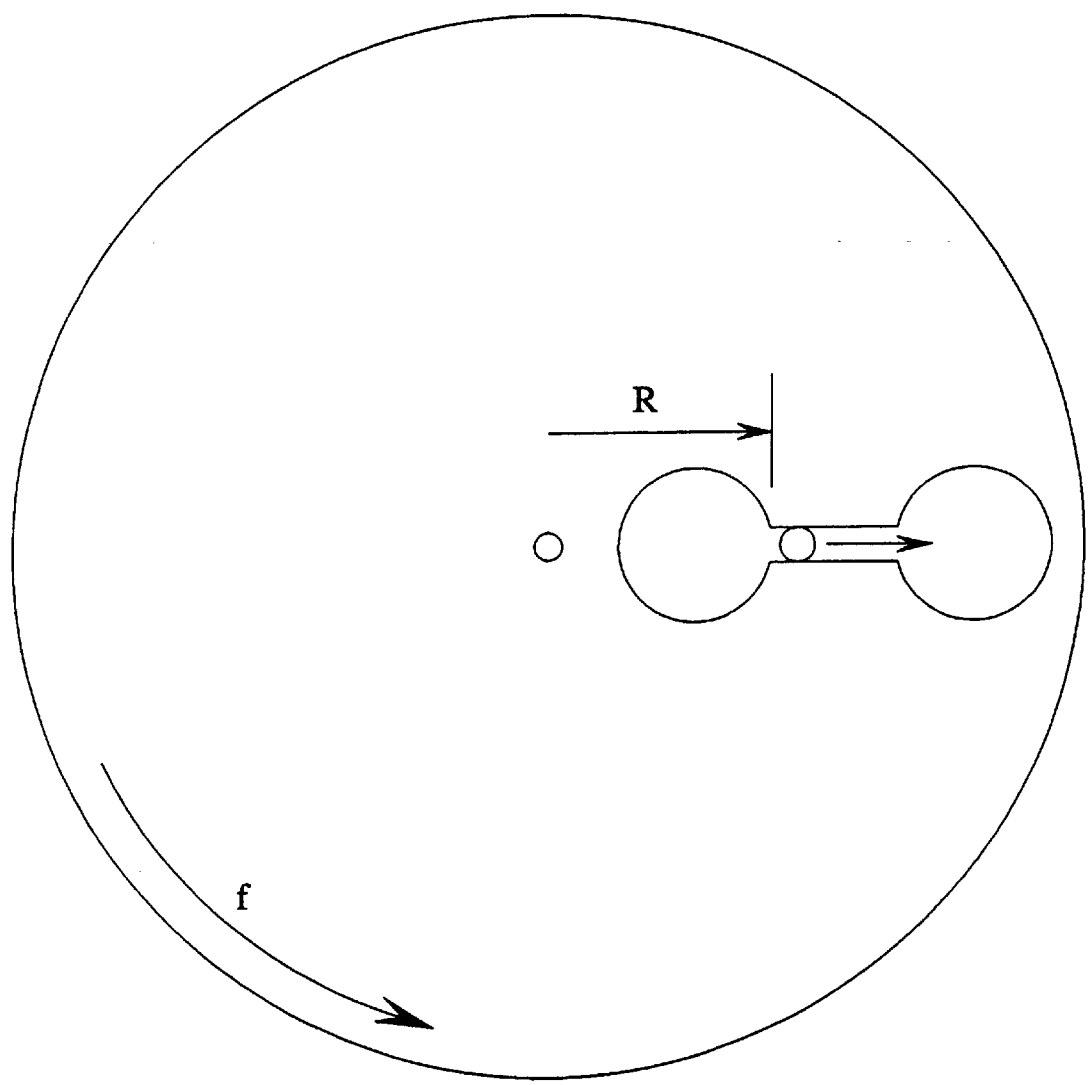
FIG. 8D is a schematic diagram of the arrangement of a channel on a disk of the invention as described with relation to Equation 23.

In FIGS. 8A, 8B and 8C, the time required to transfer 1, 10, and 100 $\mu$L droplets, respectively, through a 5 cm tube is shown. The tube connects two radially oriented reservoirs as illustrated in FIG. 8D. Transfer times are a function of radial position of the tube (0–30cm), tube diameter (10 $\mu$m, 100 $\mu$m, or 1,000 $\mu$m), and rotation frequency (100, 1,000 or 10,000 rpm). The curves shown in FIGS. 8A, 8B and 8C were calculated using Equation 23.

Taken together, these formulate and graphs describe the interrelationship of disk radii and rotation speeds, channel lengths and diameters, and fluid properties such as viscosity and density in determining fluid velocities and flow rates on the disk. The assumptions behind these derivations include viscous losses due to Poiseuille (non-turbulent) flow, with the addition of losses due to non-uniform flow of droplets and at tube inlet and outlet ports. These formulae and graphs provide lower limits for velocities and flow rates. Fluid velocities can range from less than 1 cm/sec to more than 1,000 cm/sec, and fluid flow rates from less than 1 pL/sec to tens of mL/sec for rotation rates ranging from 1 to 30,000 rpm. By combining channel diameters and positions on the disk, it is possible to carry out fluid transfer over a wide range of time scales, from milliseconds to hours and tens of hours for various processes.

C. Particular Examples of the Invention

1. Devices Using Centripetal Acceleration and Capillary Forces to Effectuate Fluid Flow Concerning the use of centripetal force to cause fluid flow in a system influenced by capillary forces, equations (5) and (8) indicate that fluid flow will begin when:

$$4\pi^2 f^2 \rho L R > \gamma \{(P_R/A_R) \cos \Theta_R - (P_T/A_T) \cos \Theta_T\} \quad (24)$$

As discussed above, Equation (24) is equivalent to Equation (6) (describing non-wetting fluid flow into a reservoir) when $\cos \Theta_{hd} T = 1$.

According to this equation, flow will not begin until a critical frequency, $f^*$, is achieved (for any particular R, L, contact angles and cross-sectional area and perimeters. This frequency increases with decreasing radial position ( as measured from the center of rotation), decreasing L (i.e., smaller reservoirs in the radial direction), and decreasing $A_T$. The choice of appropriate combinations of these variables, and materials (governing contact angles with the liquid) results in a wide varieties of critical frequencies at which fluid flow is effected.

It will be recognized that parameters in equation (24) are subject to variability inherent in analyte fluids or due to the manufacturing processes used to manufacture a centrifugal rotor or microsystems platform. This implies that there are a range of frequencies f* that exist over which fluids will flow in different copies of the same device. A properly designed centrifugal rotor or Microsystems platform manufactured according to this invention will incorporate such variations to provide reproducible fluid movement. For example, if two processes of a centrifugal rotor or Microsystems platform are to occur sequentially at frequencies f1* and f2*, the centrifugal rotor or Microsystems platform is designed according to the invention so that variability in f1* and f2* allows no overlap between the two frequencies. If f1* is 500 rpm±50 rpm, f2* cannot be 525 rpm±50 rpm because both fluids would flow, or a fluid would flow through both rotor or platform structures, at the same rotational rate. Thus, proper rotor or platform design would provide an f2* value of 700 rpm±50 rpm in a rotor or platform having an f1* value of 500 rpm±50 rpm. In this way, a centrifugal rotor or microsystems platform according to the invention can be rotated at 600 rpm providing fluid flow of a first fluid, or through a first component structure in the rotor or microsystems platform, and the rotational rate can be increased to 800 rpm to provide fluid flow of a second fluid, or through a second component structure in the rotor or microsystems platform.

Variations effecting fluid flow can also be present due to properties of the fluid, such as surface tension and density; the contact angle between the fluid and the material of the rotor or platform; and in the dimensions of the component structures (such as microchannels, capillaries, reservoirs, etc.) of the rotor or platform. In view of the definition of f* above, whatever parameter comprising f* having the largest relative variations will dominate (i.e., have the greatest influence) on the variations in f*. (Relative variations are defined for the purposes of this invention as the variation in a parameter a, termed $\Delta a$, normalized to the average or specified value of the parameter, or $\Delta a/a$) For example, variations in cross-sectional area of microchannels will have a much greater effect on variations of f* than variations in the cross-sectional area of reservoirs, due to the larger relative contribution of a small variation in a generally much smaller cross-sectional area.

The contribution of fluid densities, particularly of biological fluid samples, to the variation in rotational frequency required to effect a particular fluid flow are typically minimized by the addition of diluents having a standard density (such as water or simple buffered solutions such as phosphate buffered saline, known in the art and having a density of approximately 1 g/cm$^3$). Fluid density variations will be understood to contribute to variations in f* by only a few percent.

Surface tension variations of biological fluids are small, because these fluids are primarily comprised of water containing significant contributions of other constituents; for example, blood comprises particulates such as blood cells and platelets, as well as serum proteins, sugars, ions and other metabolites. These constituents may affect surface tension by adsorbing preferentially to the fluid surface on the rotor or microsystem platform. The concentrations of such constituents necessary to saturate a surface are very small. Because the bulk concentrations in the liquids are much larger than is necessary to saturate surfaces, variations in those bulk concentrations do not affect the amount adsorbed to the surface and hence the surface tension. Typical variations in surface tension are on the order of approximately 1–2%.

For the same reason, contact angle variations are recognized to be small contributors to variation in f* values. Additionally, adsorption of components in a fluid, particularly a complex biological sample, to a newly-presented surface during fluid flow on a rotor or Microsystems platform, will be understood to present an additional design consideration. For example, if blood is introduced into a plastic capillary, blood proteins will adsorb to the plastic surface over a period of 1–20 minutes (see Feijen et al., 1979, in *Advances in Cardiovascular Physics, vol.* 3 (Ghista et al., eds), S. Karger, Basel). This adsorption will effect the wettability and contact angle of the surface.

Variations in the dimensions of the manufactured centrifugal rotor or Microsystems platform will be understood to comprise contributions primarily in the capillaries and microchannels of said rotors and platforms. Manufacturing tolerances for conventional injection molding can routinely be held to about±13 μm, and very precise injection molding can reduce this variability to about±7 μm. For applications which require capillaries smaller than about 100 μm in diameter, manufacturing methods with even greater dimensional tolerances are preferred, such that the relative tolerances remain small. For example, precision diamond milling for the production of a mold for injection molding provides tolerances of about±1 μm, and this tolerance can be easily maintained using such molds in an injection/compression or coining machine. Similarly, deep lithographies such as LIGA may be used to create mold masters featuring component sizes in the range of 100s of μms and holding tolerances within about±1 μm. The creation of a mold is then made through transfers in ways known to those skilled in the art. Conventional photolithography may be used to produce even smaller structures, on the order of 10 microns (μms) in size, with tolerances in the range of ±0.1 μm. A new technique, termed micromilling uses microscopic tools on the order of tens of microns in size to mill patterns into plastic substrates with tolerances of ±0.1 μm, which patterns may then be transferred to a mold insert. These and other methods known to those with skill in the art can be used to prepare the rotors and microsystems platforms of the invention whereby variability in the components of the rotor or platform are minimized to produce more uniformity in the performance of the rotors or platforms.

Variations in contact angle may be controlled by treatment of the biological fluid, the surface, or both (See Benvenutti & Del Maso, 1989, in Polymers: *Their Properties and Blood Compatibility*, Kluwer Academic Publishers: Dordrecht). For example, surfaces can be pre-incubated with a solution of serum albumin to "pre-block" the surface with a homogeneous protein solution and thereby prevent adsorption of serum proteins from blood samples. (Benvenutti & Del Maso, Id.) The presence of these proteins on the surface thus stabilizes the contact angle when the surface is in contact with a complex, protein-containing solution such as blood. Fluid treatment can alternatively be effected by the addition of a component that binds to the surface in preference to adsorption of biological fluid components. Additional modifications include heparinization of the surface, or the addition of heparin to the biological fluid, for example, in order to prevent coagulation; addition of heparin is, of course, required in embodiments of methods of using the rotors and microsystems platforms of the invention directed towards, for example, separation of blood components.

Another consideration affecting variation in contact angle is nonhomogeneity in the surface due to variations of the surface "roughness" at the microscopic level. These variations produce hysteresis in the contact angle over a range through which the contact angle varies. The contribution of hysteresis is significant because the maximum contact angle in this range will determine the pressure (and hence rotational speed) at which fluid flow will occur through a capillary structure. This range will be a characteristic of the manufacturing process, and will be understood to contribute variation in $\cos \Theta$ of no more than approximately 1–2%.

The dominant source of variation in f* is that which has the largest variation. Variations in contact angle and surface tension are on the order of 1–2%. If variations in the capillary cross-sectional dimensions are greater than 1–2%, frequency variations will arise due to these variations in dimension, and will be related by the equation: $\Delta f^*/f^* = (\Delta a/a)^{1/2}$.

In the construction of the microsystems platforms and rotors of the invention, it will be recognized that a fluid-impermeable lid or cover over the first platform surface is necessary, because fluid must be confined to a capillary junction in order for centripetal and capillary forces to be useful in controlling fluid flow. Methods by which such lids or surface coverings can be attached to the surface of the platforms or rotors of the invention include screen-printable ultraviolet light cure-utilizing utilizing methods, pressure-sensitive sealing methods, or heat-cured glues or epoxies. Also useful are spin coating such adhesives from a solution onto the lid material using conventional photolithography; the use of self-adhering films or heat-sealable films; as well as ultrasonic welding. Dimensional tolerances required for such lid-welding methods are expected to provide a minimum of about±2.5 µm, while certain of these methods will advantageously produce even better tolerances.

In one non-limiting example, a volume of 100 µL of water is sequentially moved from a reservoir near the center of a rotating disk towards the edge of the disk. All parts are manufactured from a single material having a contact angle of 100° (>90°, therefore non-wetting with water). The surface tension of water is $\gamma=72$ dyne/cm² and the density is $\rho=1$ g/cm³. Rectangular reservoirs and tubes having width W and thickness T are arranged along the radial direction of the disk. Reservoirs having the dimensions listed in the Table below are located at radial positions R, having the following critical frequencies:

TABLE I

| R(cm) | $W_R$(cm) | $T_R$(µm) | $W_T$(µm) | $T_T$(µm) | f(rpm) |
|---|---|---|---|---|---|
| 2 | 1 | 0.1 | 150 | 150 | 929 |
| 3.5 | 1.5 | 0.1 | 110 | 110 | 1006 |
| 5 | 2 | 0.1 | 80 | 80 | 1142 | where water flows from each reservoir into the tube connecting it with the next reservoir at the given frequency and when $P_R=2.2$ cm, $A_R=0.1$ cm², $T_T=0.06$ cm and $A_T=2.25\times 10^{-4}$ cm²; when $P_R=3.2$ cm, $A_R=0.15$ cm², $T_T=0.044$ cm and $A_T=1.21\times 10^{-4}$ cm²; and when $P_R=0.5$ cm, $A_R=0.5$ cm², $T_T=0.032$ cm and $A_T=0.64.\times 10^{-4}$ cm².

Figure 9:
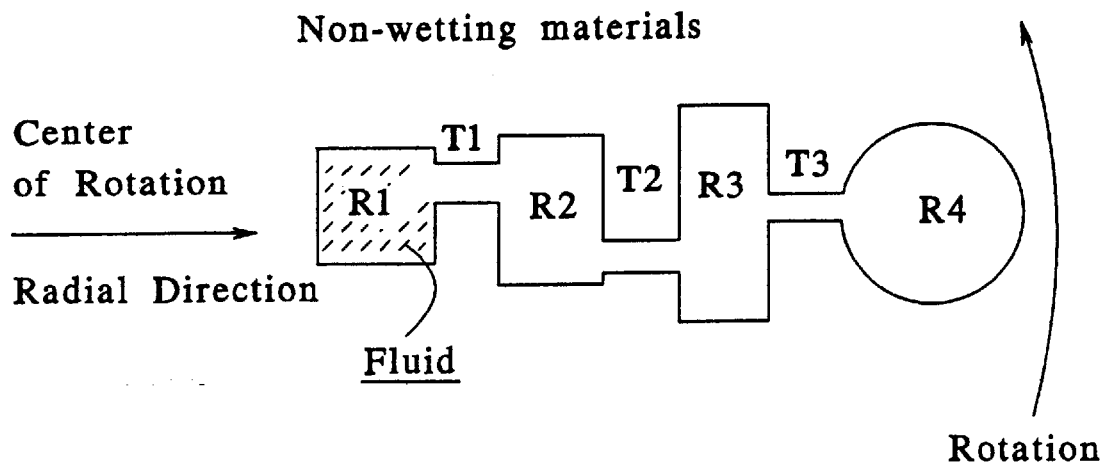
FIG. 9 is a schematic of the time-dependent fluid movement in a Microsystems platform constructed of a nonwetting material.

FIG. 9 illustrates this sequence of fluid motion. In this example, fluid is placed in the first reservoir closest to the center of rotation. By using Equation (6) it is determined that fluid is expected to flow from the first reservoir through the first tube at a rotational frequency of at least 929 rpm but less than 1006 rpm. By rotating the disk at between 929 rpm and 1005 rpm, the fluid flows from the first reservoir into the first tube or channel, and then empties into the second reservoir; this is because the pressure needed to traverse the interface between the first tube and the second reservoir is less that the pressure generated at that point on the disk when the disk is accelerated to at least 929 rpm but less than 1006 rpm. This description is also understood in terms of the equations presented above; fluid will flow when the pressure at this position on the disk and at this rotational rate as expressed by Equation (5) is greater that the pressure due to capillary forces as expressed in Equation (5). Upon flowing into the second reservoir, however, capillary forces halt fluid flow, because the pressure needed to traverse the interface between the second reservoir and the second tube is more that the pressure generated at that point on the disk when the disk is accelerated to at least 929 rpm but less than 1006 rpm. By increasing the rotation rate to 1006 rpm, the fluid is motivated to flow from the second reservoir into the second tube or channel, and then empties into the third reservoir; this is because the pressure needed to traverse the interface between the second tube and the third reservoir is less than the pressure generated at that point when the disk is accelerated to 1006 rpm. Upon flowing into the third reservoir, however, capillary forces again halt fluid flow, because the pressure needed to traverse the interface between the third reservoir and the third tube is more than the pressure needed to traverse the interface between the third reservoir and the third tube is more than the pressure generated at that point on the disk when the disk is accelerated to 1006 rpm. By increasing the rotation rate to 1142 rpm, fluid flows from the third reservoir into the third tube or channel, and then empties into the fourth and last reservoir.

Ranges of tube/channel architecture and rotational speed are greatly increased for surfaces that are more hydrophobic. This principle is illustrated for a microplatform disk as shown in FIG. 9, comprising a material having a contact angle of 110°;

TABLE II

| R(cm) | $W_R$(cm) | $T_R$(cm) | $W_T$(µm) | $T_T$(µm) | f(rpm) |
|---|---|---|---|---|---|
| 2 | 1 | 0.1 | 250 | 250 | 707 |
| 3.5 | 1.5 | 0.1 | 150 | 159 | 854 |
| 5 | 2 | 0.1 | 100 | 100 | 1015 | where water flows from each reservoir into the tube connecting it with the next reservoir at the given frequency.

Other non-limiting examples include:

1. Microplatforms and other microsystems fabricated of a single material having a contact angle of <90°. Due to the dependence of the pressure in Equations (5) and (7) on trigonometric functions, the sign of the pressures changes, reflecting the fact that the surfaces of the device preferentially wet with fluid. As a result, fluid is drawn by capillary action from the large reservoir into the tube of smaller cross-sectional area. If fluid motion into the second reservoir results in a decrease in the amount of the wetted surface, capillary forces will act to oppose further flow, forming a capillary action valve analogous to those discussed above. Pressure must then be applied to initiate further flow. Reservoir and tube geometry (such as sharp exit tips on the channel) are use to ensure the need for positive pressure for the fluid to enter the second reservoir. Thus, arrangement of the component geometries, and choice of material and contact angles, permit selective and differential fluid flow between reservoirs and reaction chambers via connecting channels.

2. Centrifugal rotors, microplatfonms and Microsystems arc also fabricated comprising material having contact angles <90° and other material having contact angles >90°. For example, using aqueous solutions a fluid reservoir may be hydrophilic (contact angle <90°), whereas a tube or channel is fabricated from a material having a contact angle >90° (thereby requiring positive pressure to be applied to motivate fluid flow from the reservoir into the channel).

3. Reservoirs and channels are also provided in certain embodiments of the invention having variable cross-sectional area and/or perimeter in the direction of fluid flow (e.g., radially in a microplatform disk system). As fluid flow, the position of solid-liquid-vapor contact also move; as the cross-sectional areas change, the pressures defined in Equation (1) change as well, changing the magnitude of total capillary forces. An advantage of such design is that the rate of fluid flow in the channel can be more precisely controlled. For example, channels can arrayed on a platform whereby the force opposing fluid flow increases with distance form the center of the platform, thereby requiring increased rotational speed to overcome such forces as fluid flows through the system.

4. Relatively large-scale (i.e., micron-size) imperfections are provided on the interior of tubes or reservoirs, to provide directionality of fluid flow, to limit fluid velocity, or to otherwise control flow. (See Columbus and Palmer, 1987, *Clinical Chemistry*) 33 1531.

b. Devices Using Centripetal Acceleration and Capillary Forces to Meter Fluid

The invention provides means for producing aliquots of a fluid from a reservoir or other fluid chamber or channel. Such aliquots are provided by a combination of centripetal acceleration and capillary action and are dependent on the geometry of the ends of the reservoirs and channels. The provision of aliquots is illustrated by the following example. Pressure is applied to a fluid to motivate the formation of a droplet at an opening to a reservoir or at the end of a channel, as described by Equation (6) above. The volume of a droplet formed at a given pressure is then calculated using Equations (7) and (8) as follows:

$$\rho V a_c = \rho V \omega^2 R = k(2\pi r \gamma)$$

$$V = (kr\gamma)/(2\pi \rho f^2 R) \quad (25)$$

For a tube or channel having a diameter of 200 $\mu$m (corresponding to a radius of 100 $\mu$m), droplets with a volume of 1 $\mu$L are released when subjected to an acceleration of 5 g (for a value of the constant k=1). Acceleration of this magnitude is achieved by rotation at 470 rpm for a reservoir or channel positioned 2 cm from the center of rotation. Because droplets form at a finite rate ( a rate determine by the geometry of the fluidics system, the contact angle (determined by the material from which the microsystem is fabricated), and the fluid density), rotational speed can be adjusted to the critical frequency for a time sufficient for a single droplet to be delivered, followed thereafter by a reduction in rotational speed.

Figure 10:
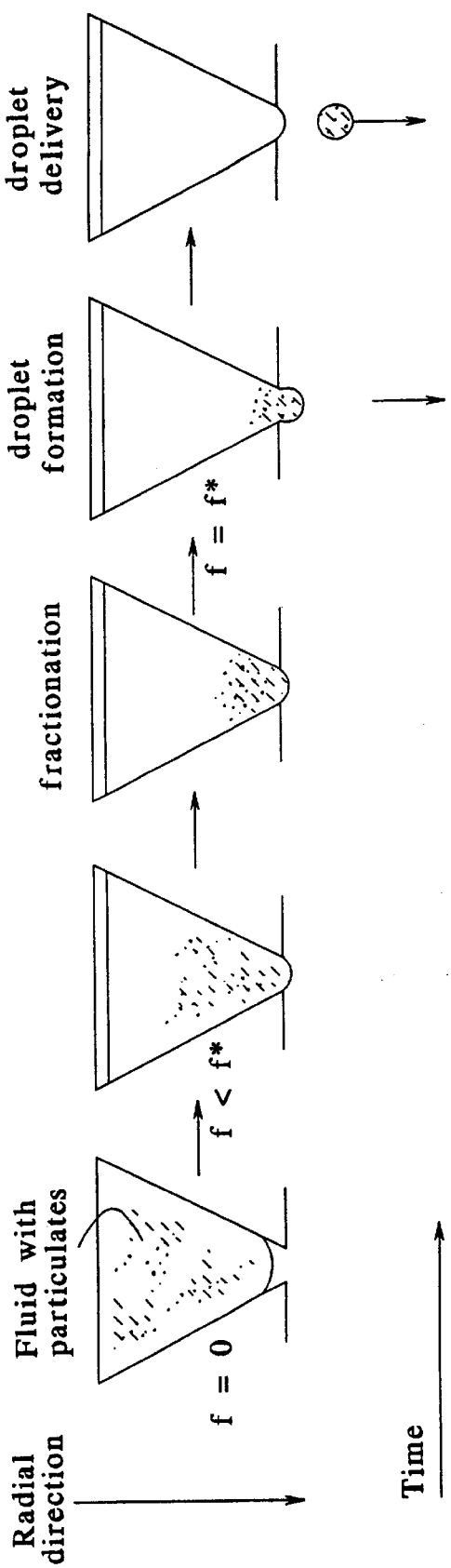
FIG. 10 illustrates schematically the geometry of droplet formation for enriching particulates in a suspension.
Figure 11A:
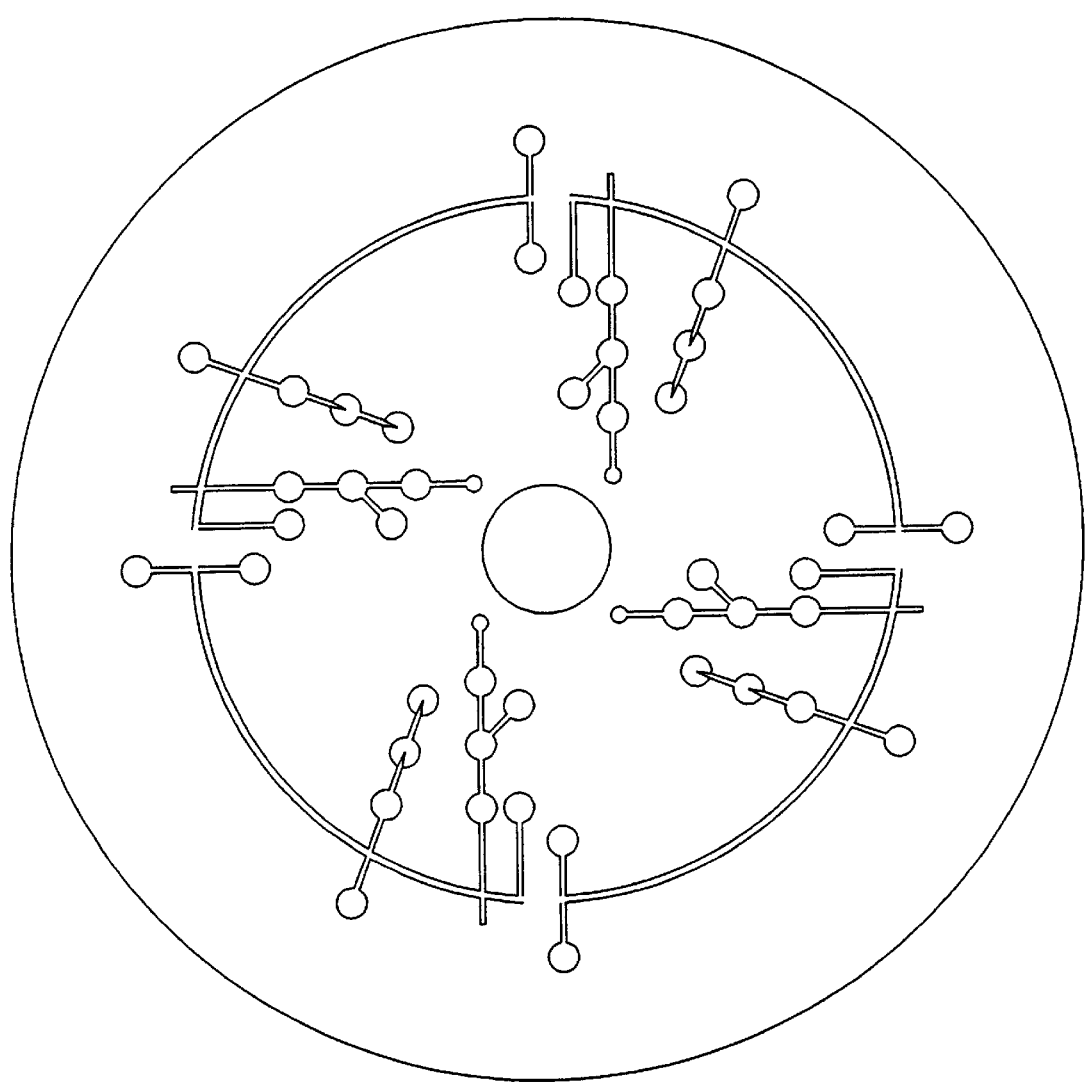
FIGS. 11A through 11E are schematic diagrams of the different structural and functional layers of a disk of the invention configured for DNA sequencing.
Figure 11B:
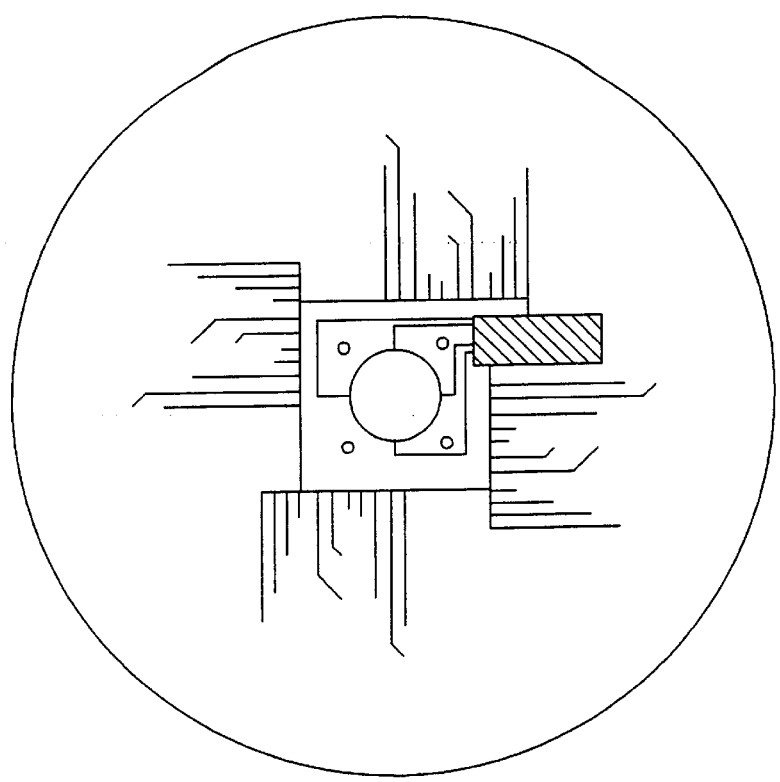
Figure 11B:
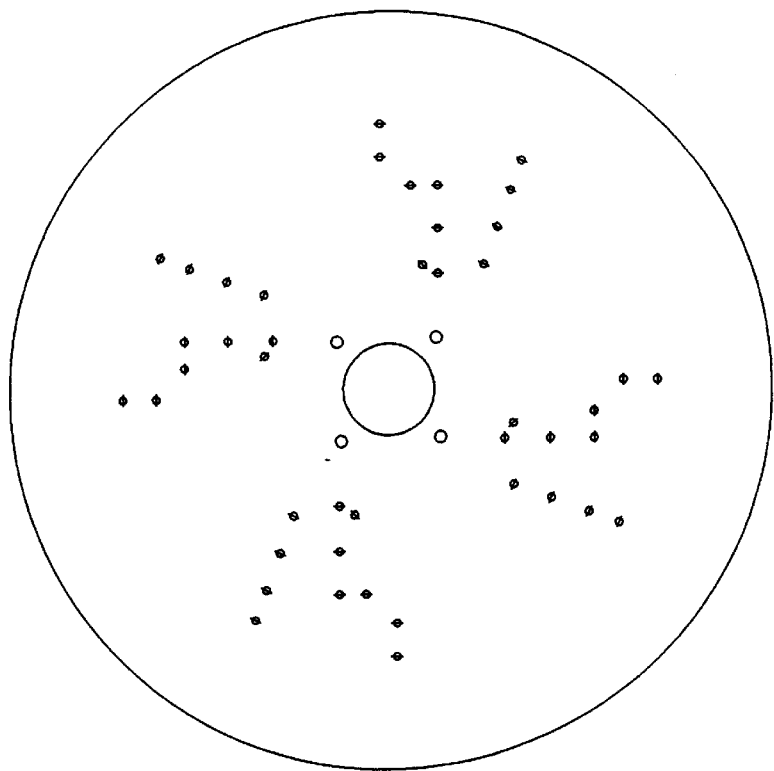
Figure 11C:
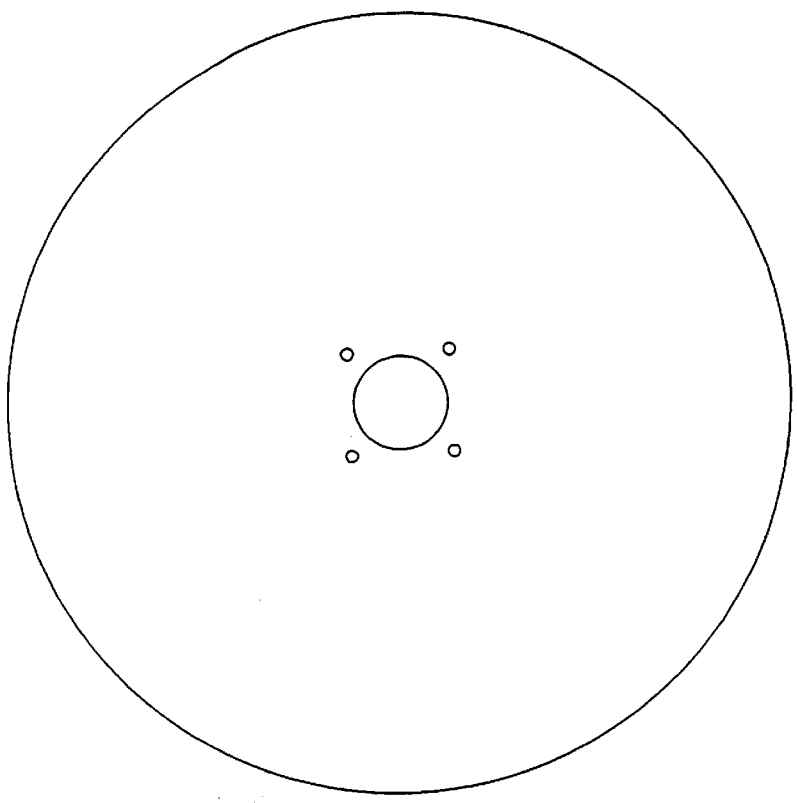
Figure 11C:
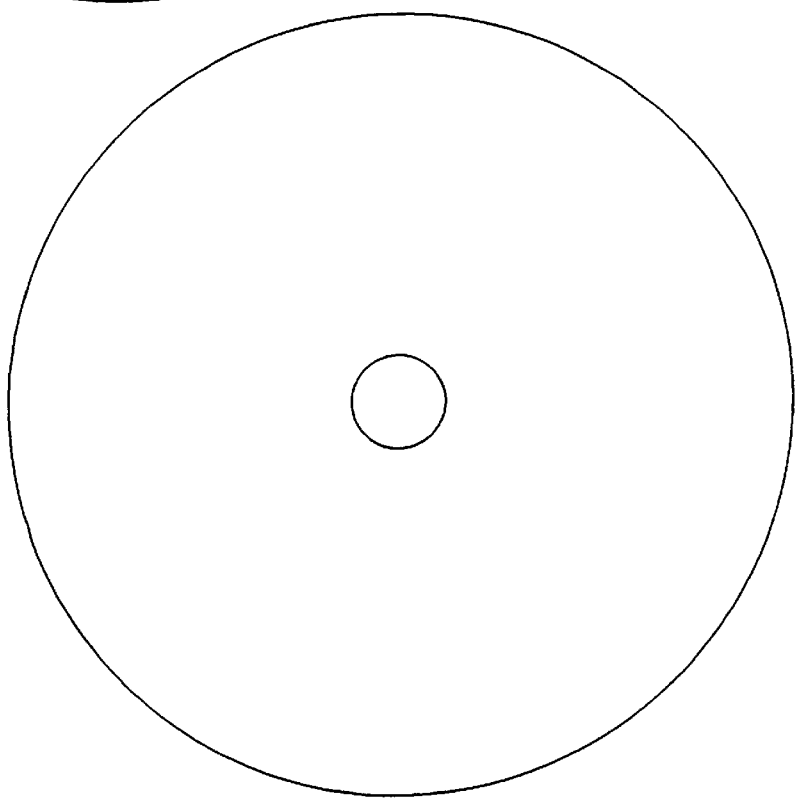
Figure 11D:
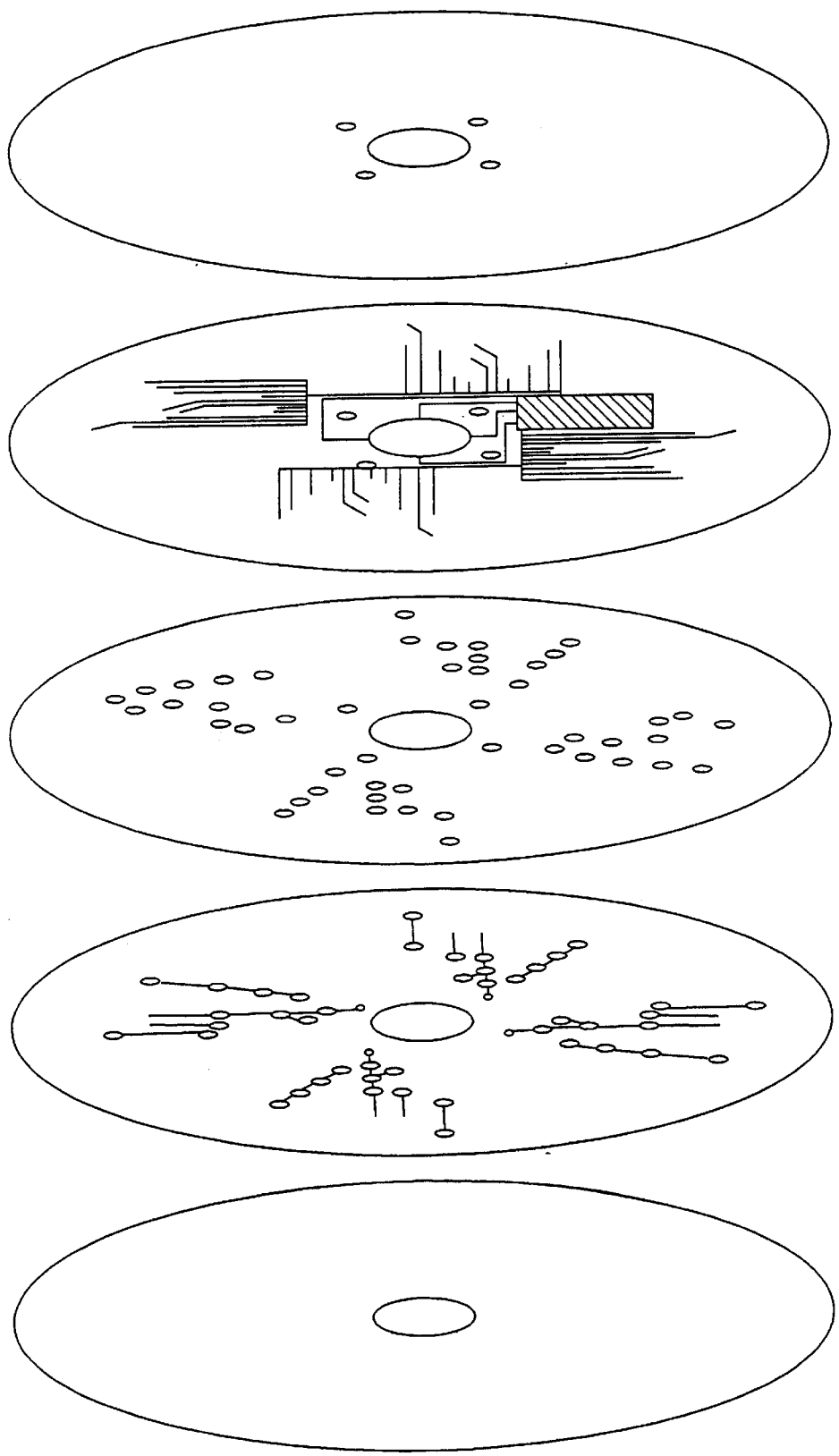
Figure 11E:
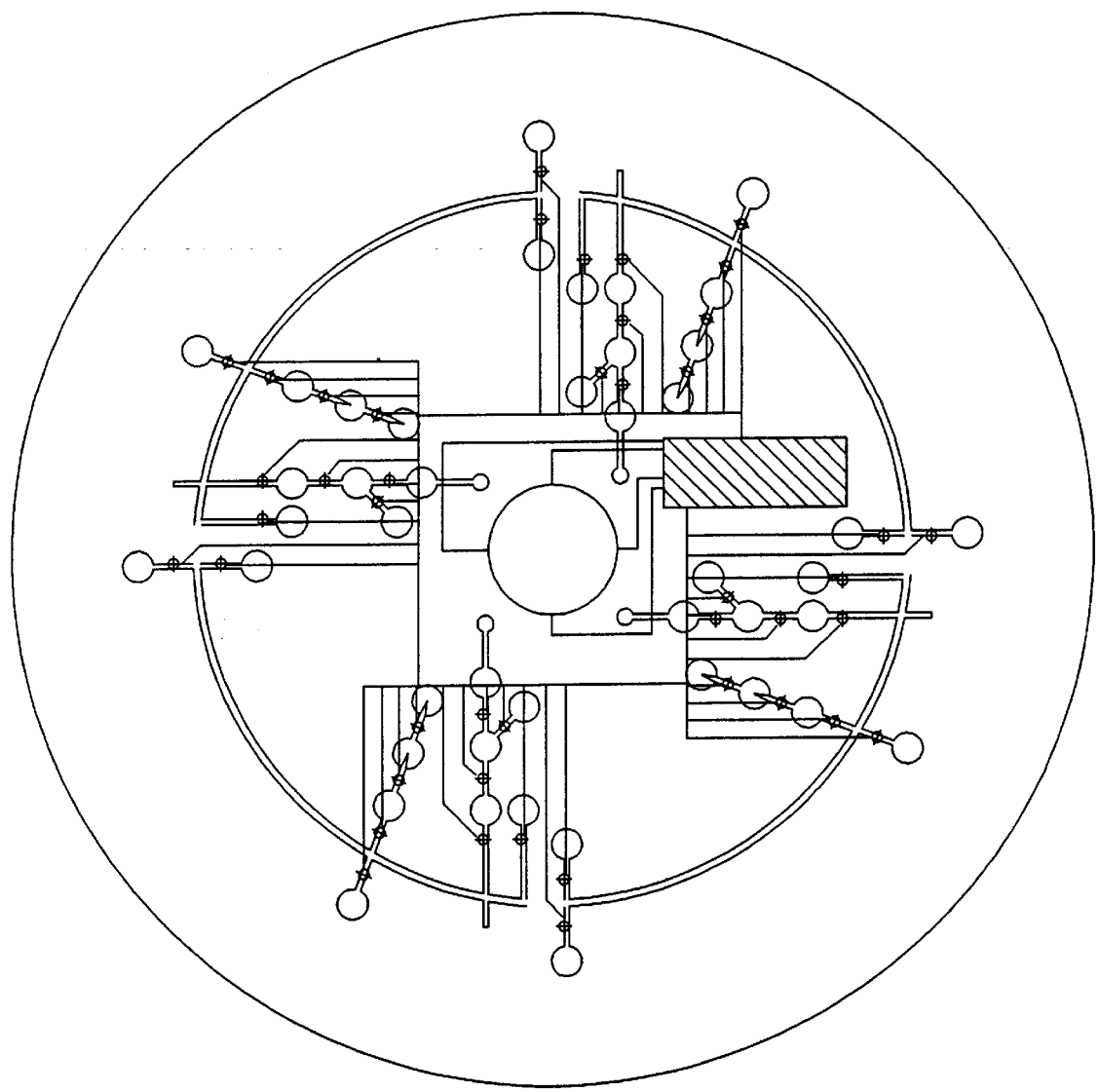

Droplets form at a finite rate determined by the geometry of the fluidics system, the contact angle, surface tension, fluid density and pressure supplied by rotation of the disk. The relationship between droplet formation and these parameters can determined (see Adamson, Id.)

c. Devices Using Centripetal Acceleration and Capillary Forces to Produce and Deliver Enriched Droplets The invention also provides means for producing aliquots of a fluid from a reservoir or other fluid chamber or channel, wherein the droplet contains a concentration of particulates contained in the fluid. This aspect of the invention is illustrated in FIG. 10 for a simple fractionation aliquot dispensing system made from non-wetting material. A solution containing a fluid and particulates (such as cells, for example) is introduced into a conical reservoir that empties through a sharp "tip" or constriction at one end of the direction of fluid flow into a larger chamber, the tip having a small diameter relative to the conical reservoir. Rotation at a frequency below the critical frequency necessary for movement of fluid through the orifice as a droplet results in concentration of the particulates at the end of the conical reservoir, i.e., at the position of the sharp tip. (This is analogous to conventional centrifugation performed at a microscopic scale.) A droplet containing a concentration of the particulates is then produced by increasing the rotation rate to the critical frequency for a time sufficient to produce the droplet. The droplet produced has a volume given by Equation (10); from the volume of the droplet and the concentration of the particulates in both the original fluid and after production of the droplet the concentration of the particulates in the droplet is determined. Alternatively, means such a spectrophotometric means may be used to determine concentration, as described in International Application WO97/21090, incorporated by reference herein.

An advantage of using conical reservoir for a non-wetting fluid levels in the reservoir (because the ratio of the area of the liquid-vapor and liquid-solid interface decreases). As a result, the magnitude of the pressure required to produce a droplet (and the critical frequency) increases with the production of a droplet. This ensures that only a single droplet is produced, absent an increase in rotational speed.

It will be recognized that the surface tension of the fluid will vary depending on the concentration of particulates, an extreme example being the presence of detergents or surfactants in the solution. Detergents and surfactants decrease surface tension to a reproducible value when present in very dilute quantities, producing no important impediment to operation of the device. Particulates affect surface tension through a colligative effect (reducing surface tension as concentration of particulates is increased). This characteristic can be used to increase droplet formation under circumstances where particulates (such as cells) are concentrated or enriched at the exit orifice of a passage: rotation at a speed below the threshold for bulk fluid flow may provide pressure on a concentrated solution comprising particulates sufficient for droplet formation to occur.

It will be recognized that the above theoretical consideration and mathematical formulae will deviate with expected deviations from ideality; such deviation are within the skill of a worker of ordinary skill to determine without undue experimentation. One example of a expected deviation from ideality is a consequence of neglecting the influence of gravity on fluid flow in the above theoretical discussion. The effect of gravity is in turn dependent on the geometry of the microstructure: in axis of rotation being typically vertical, gravity acts perpendicular to the direction of fluid flow and is expected to have a negligible effect over typical fluid densities and viscosities (e.g., using aqueous solutions). Contact angles are affected by adsorption of solution components (such as proteins); it is known, however, that the creation of microscopic irregularities in the reservoir and tube (or channel)wall make such variation in contact angle virtually unimportant (see Columbus and Palmer, ibid.). Orifice shape, fluid density and other variables also influence the specific dynamics of fluid flow. It is also known that surfaces can be treated to prevent adsorption of solution components, using methods such as silation and plasma treatment.

Because the flow restriction devices of the invention do not involve physical "closing" of valves, the following additional consideration exist: evaporation, condensation and aerosol production in liquids valved by the invention. Evaporation is a concern in long-term storage of devices comprising liquids whose fluid flow is to be controlled using the valves of the invention. Condensation issues similarly arise for devices stored comprising dry reagents which must not be prematurely wetted due to adsorption of water or other fluids that condense upon temperate changes or otherwise. Either of these potential difficulties can be addressed by the placement of a thin film of poly(ethylene oxide) or glycerine within the capillaries of the devices comprising the microvalve of the invention, which would provide an effective barrier to water vapor and aerosols. Such barriers are also advantages because bulk fluid flow dissolves the barrier, and the amount of such barrier material used is sufficiently small that its presence in the analytic fluid is inconsequential (e.g., 0.1–1.0 microlitres).

Aerosol production can be reduced using channels having sharp curves (such as "U" tubes) or other curved, serpentine designs.

It will also be recognized that liquid contact with surface material such as certain plastics can cause swelling of the material due to diffusion of the fluid into the material. This is particularly significant in plastic that are wetted by specific fluids such as water. Such swelling could change the cross-sectional areas of the invention. Swelling can be reduced by surface coating, e.g., with silicone oxides or polymer laminates. Swelling can also be an expected part of the design of such systems: assuming that the shelf-life of a product is known, the degree of swelling over the lifetime of the product can be properly estimated and the shape and configuration of the microsystem can be designed to minimize the effects of swelling.

EXAMPLE 1

Fabrication of Microplatform Disks for Chemical Analysis, Synthesis, and Applications Microplatform disks of the invention are fabricated from thermoplastics such as teflon, polyethylene, polypropylene, methylmethacrylates and polycarbonates, among others, due to their case of molding, stamping and milling. Alternatively, the disks can be made of silica, glass, quartz or inert metal. A fluid handling system is built by sequential application of one or more of these materials laid down in stepwise fashion onto the thermoplastic substrate. FIGS. 11A through 11E are a schematic representation of a disk adapted for performing DNA sequencing. Disks of the invention are fabricated with an injection molded, optically-clear base layer having optical pits in the manner of a conventional compact disk (CD). The disk is a round, polycarbonate disk 120 mm in diameter and 100 pm thick. The optical pits provide means for encoding instrument control programming, user interface information, graphics and sound specific to the application and driver configuration. The driver configuration depends on whether the micromanipulation device is a hand-held, benchtop or floor model, and also on the details of external communication and other specifics of the hardware configuration. This layer is then overlaid with a reflective surface, with appropriate windows for external detectors, specifically optical detectors, being left clear on the disk. Other layers of polycarbonate of varying thickness are laid down on the disk in the form of channels, reservoirs, reaction chambers and other structures, including provisions on the disk for valves and other control elements. These layers can be prefabricated and cut with the appropriate geometries for a given application and assembled on the disk. Layers comprising materials other than polycarbonate can also be incorporated into the disk. The composition of the layers on the disk depend in large part on the specific application and the requirements of chemical compatibility with the reagents to be used with the disk. Electrical layers can be incorporated in disks requiring electric circuits, such as electrophoresis applications and electrically-controlled valves. Control devices, such as integrated circuits laser diodes, photodiodes and resistive networks that can form selective heating areas or flexible logic structures can be incorporated into appropriately wired recesses, either by direct fabrication of modular installation onto the disk. Reagents that can be stored dry can be introduced into appropriate open chambers by spraying into reservoirs using means similar to inkjet printing heads, and then dried on the disk. A top layer comprising access ports and air vents, ports or shafts is then applied. Liquid reagents are then injected into the appropriate reservoirs, followed by application of a protective cover layer comprising a thin plastic film.

EXAMPLE 2

Fluid Metering Microsystems Platform

Figure 12:
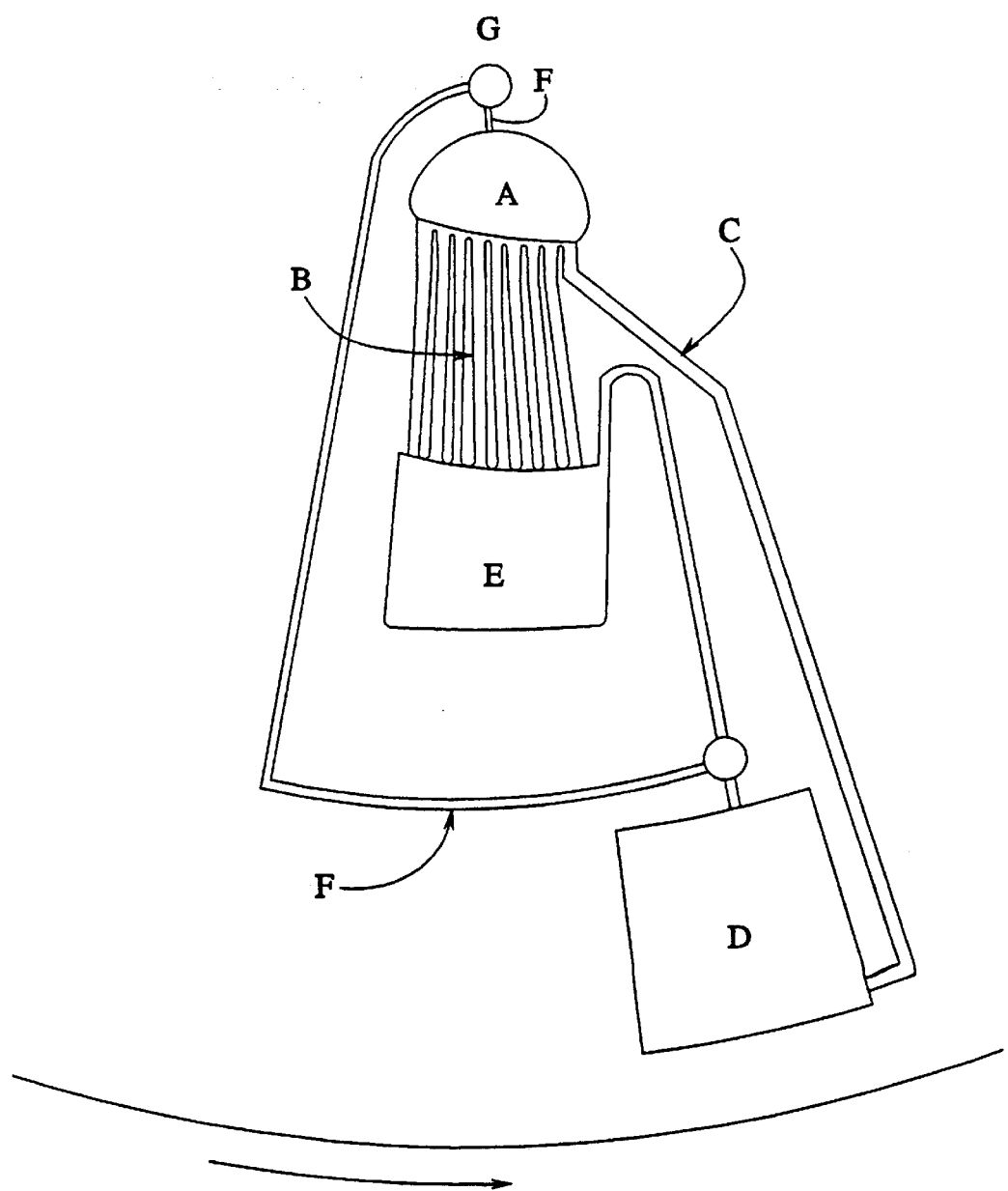
FIG. 12 is a schematic diagram of a platform of the invention comprising a metering capillary as described in Example 2.

A microsystem platform is constructed as described in Example 1 from components having a contact angle less than 90° for all fluids to be applied to the platform, and having components arrayed on the platform to provide metered fluid delivery to a fluid chamber in a defined volume. A diagrammatic representation of this platform is shown in FIG. 12.

An entry port A having a depth in the platform surface from about 0.25 mm to about 1 mm and lateral dimensions of from about 0.2 cm to about 2 cm is constructed on the platform fluidly connected with a metering capillary B having a cross-sectional diameter of from about 0.02 mm to about 0.75 mm and proximal ends rounded with respect to entry port A. The entry port is also constructed to be fluidly connected with an overflow capillary C having a cross-sectional diameter of from about 0.02 mm to about 0.75 mm and proximal ends rounded with respect to entry port A. The overflow capillary is fluidly connected with an overflow chamber D having a depth in the platform surface greater than the depth of the overflow capillary C and that ranges from about 0.02 mm to about 1 mm. Metering capillary B is fluidly connected to fluid chamber E having a depth in the platform surface greater than the depth of the metering capillary B and that ranges from about 0.02 mm to about 1 mm. Each of the overflow and fluid chambers is also connected with air ports or air channels, such as F, that have dimensions of about 0.02 mm to about 1 mm and permit venting of air displaced by fluid movement on the platform. A capillary junction G is present in the air channel to prevent fluid flow into the air channel.

Entry port A is positioned on the platform from 1 cm to 20 cm from the center of rotation. Metering capillary B extends from entry port A from about 0.5 cm to about 1 cm. The extent of the length of overflow capillary C is at least about 20% greater than the extent of the length of metering capillary B. The position of fluid chamber E is from about 0.5 cm to about 10 cm from the center of rotation, and the position of overflow chamber D is thus from about 1.5 cm to about 11.5 cm from the axis of rotation.

In the use of this platform, an imprecise volume (ranging from 1–150 μL of fluid) of a fluid is applied to the entry port A. In embodiments of the platform comprising air displacement channels, the fluid will wick into air channel F. The presence of the capillary junction G in air channel F prevents fluid flow into the air channel. Fluid also wicks into metering capillary B and overflow capillary C. Fluid flows through the metering capillary B and overflow capillary C at no rotational speed until the fluid reaches capillary junctions at the junction between metering capillary B and fluid chamber E and overflow capillary C and overflow chamber D. Metering capillary B is constructed to define a precise volume from about 1–150 μL of fluid between entry port A and the capillary junction at fluid chamber E, which is designed to be at least the amount of the fluid placed by the user in entry port A.

After sample loading by a user and filling of metering capillary B and overflow capillary C at no rotational speed, the platform is spun at a first rotational speed ranging from 10–500 rpm; the exact value is dependent on the position of the components on the platform. For example, for an entry port A having a depth of 0.6 mm, metering capillary B having dimensions of 0.5 mm×0.5 mm in cross-section and a length of 2.2–3.8 cm from the center of rotation, overflow capillary C having dimensions of 0.5 mm×0.5 mm in cross-section and a length of 5.4 cm from the center of rotation, this first rotational speed is equal to 128 rpm for either water or milk.

Due to the greater distance of the end of overflow capillary C from the center of rotation than the end of metering capillary B, fluid flows through overflow capillary C into overflow chamber D. The platform is spun until all excess fluid is evacuated from entry port A and into overflow chamber D, except the fluid contained in metering capillary B.

At a second rotational speed that is greater than the first rotational speed, typically in the range of 100–2000 rpm, the precise amount of fluid contained in metering capillary B is delivered into fluid chamber E. For example, for an entry port A having a depth of 0.6 mm, metering capillary B having dimensions of 0.5 mm×0.5 mm in cross-section and a length of 2.2–3.8 cm from the center of rotation, overflow capillary C having dimensions of 0.5 mm×0.5 mm in cross-section and a length of 5.4 cm from the center of rotation, this second rotational speed is equal to 400 rpm for either water or milk.

EXAMPLE 3

Fluid Displacing Microsystems Platform

A microsystem platform is constructed as described in Example 1 having a contact angle greater than or less than 90°, and having components arrayed on the platform to provide fluid displacement from a first fluid chamber to a third fluid chamber using a displacement fluid contained in a second fluid chamber.

Figure 13:
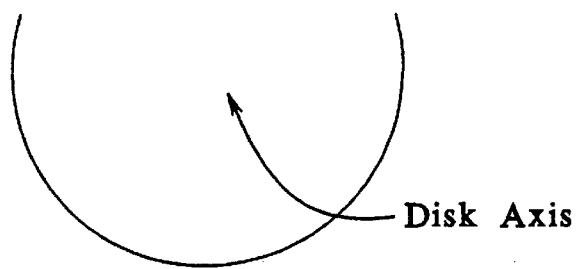
FIG. 13 is a schematic diagram of a platform of the invention comprising fluid displacement by laminar flow as described in Example 3.
Figure 13:
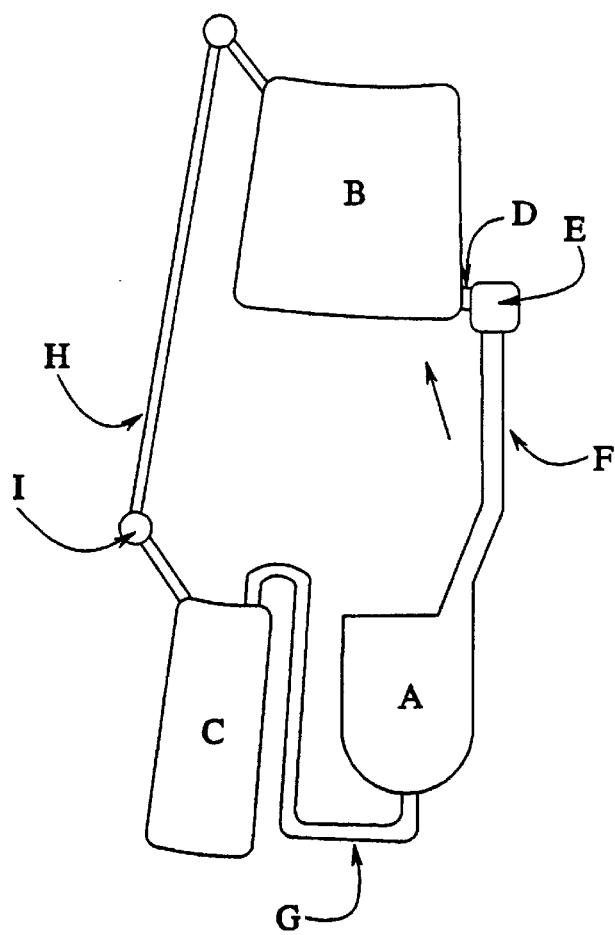
Figure 13:
Figure 14:
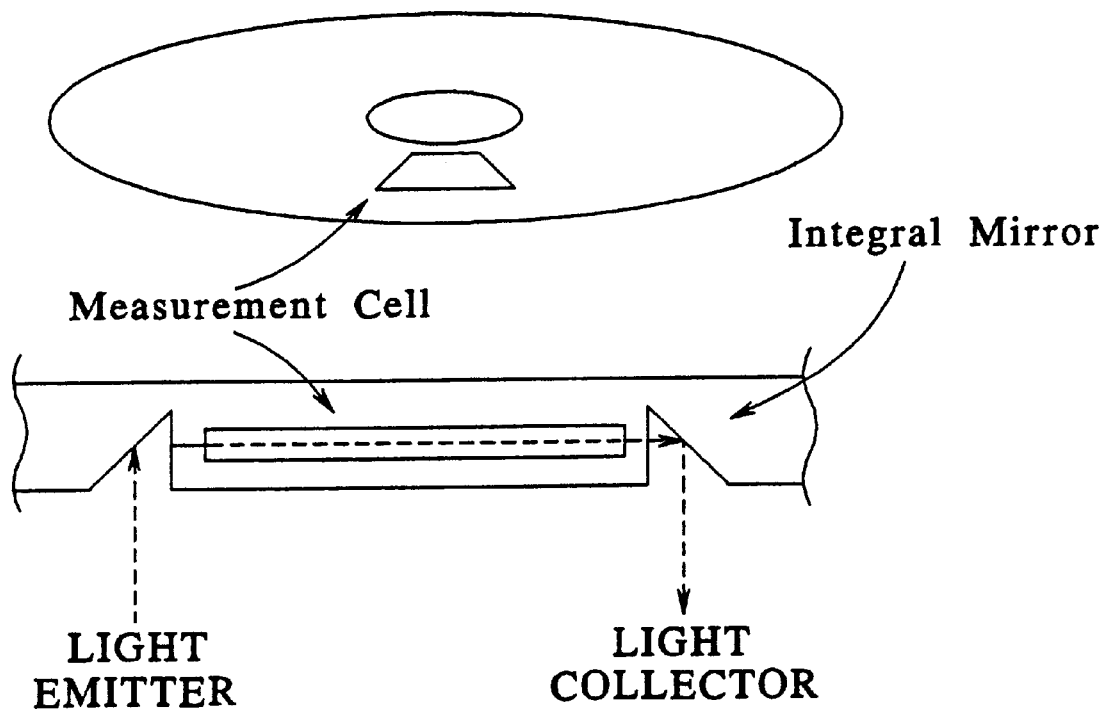
FIG. 14 is a schematic diagram of the spectrophotometric chamber described in Example 4.

Three fluid chambers A, B and C are arrayed on the platform as shown in FIG. 13. Each chamber ranges in depth in the surface of the platform from about 0.25 mm to about 1 mm and lateral dimensions of from about 0.2 cm to about 2 cm. A capillary D leading from fluid chamber B has a cross-sectional diameter of from about 0.02 mm to about 0.75 mm. A capillary junction E is fluidly connected with capillary D and has dimensions at least as deep and wider than capillary D. A flow channel F having cross-sectional dimensions of from about 0.02 mm to about 0.75 mm is fluidly connected to capillary junction E and with fluid chamber A. A capillary G is fluidly connected to both fluid chambers A and C and has cross-sectional dimensions of from about 0.02 mm to about 0.75 mm. Also provided on the platform are air ports and channels H and K, optionally comprising capillary junction I to prevent fluid flow through the air channels.

This collection of components is positioned on the platform from about 1 cm to about 20 cm from the center of rotation. In the arrangement of these components, fluid chamber A is radially positioned farther from the center of rotation relative to fluid chamber B. Capillary G comprises a path so that fluid flow passes through the capillary at a point closer to the center of rotation than the inward extent of fluid chamber A. Fluid chamber C may be positioned at the same radius as chamber A or more distantly from the center of rotation.

Fluid chamber B is charged with displacement fluid, typically on manufacture or in preparation of the platform for use. Fluid chamber A usually contains a fluid sample, introduced directly or using metering capillaries as described in Example 2 or otherwise; such combinations of the components of the platforms of the invention are within the skill of those with skill in the art to combine. The volume of displacement fluid in fluid chamber B is typically greater than the volume of sample fluid in fluid chamber A. Upon rotation of the platform at a rotational speed F1, which ranges from about 50–3000 rpm, displacement fluid flows through capillary D, capillary junction E, flow channel F and into fluid chamber A. Because of the dimensions of the components of the platform, fluid flow is laminar. In response to fluid flow of displacement fluid into fluid chamber A, the sample fluid in chamber A flows through capillary G and into fluid chamber C. The geometry of capillary G ensures that fluid chamber A remains filled at all times during displacement of sample fluid into fluid chamber C. Fluid flow proceeds with rotation of the platform until all sample fluid in chamber A is replaced by displacement fluid, and sample fluid is dispensed into fluid chamber C. Because of laminar fluid flow, very little mixing of sample fluid and displacement fluid occurs.

EXAMPLE 4

Increase in Optical Pathlength Using Integral Mirrors in a Rotating Microplatform for Performing Spectrophotometric Measurements Spectrophotometric measurements in centrifugal rotors or microsystems platforms encounter limitations relating to relatively short pathlengths across such Microsystems platforms or through microanalytical rotors. Since the amount of light absorbed by a solution at any wavelength is directly proportional to both the depth of the absorbing layer (i.e., the spectrophotometric pathlength) and the concentration of the absorbing molecules (the Lambert-Beer law), improvements in spectrophotometric measurement over a range of solution concentrations of absorbing molecules can be addressed through increasing the pathlength through the absorbing solution.

In a microsystem platform according to this invention and as disclosed in International Application No. WO97/21090, the top-to-bottom pathlength is extremely abbreviated, typically ranging from about 0.1 mm to about 1 mm. However, such a platform can also present a relatively wide lateral aspect (see FIG. 12). As a result, spectrophotometric measurement can be improved by increasing the pathlength in the lateral dimension.

This embodiment of the invention is illustrated in FIG. 12. Light from a spectrophotometric light source, typically at a particular wavelength, is shone perpendicularly on the surface of the platform or rotor. The platform or rotor comprises a measurement cell having optically transparent side walls embedded in and perpendicular to the plane of the platform surface. In optical proximity to the transparent sidewalls of the measurement chamber is a first mirror, angled at a 45° angle to the plane of the transparent sidewalls, wherein the mirror is embedded in the surface of the platform or rotor and is either exposed to or covered by an optically-transparent portion of the surface of the platform. The spectrophotometric light source is positioned perpendicularly relative to the plane of the surface of the platform and in a position to illuminate the first mirror. Light is reflected from the first mirror, through the transparent sidewall on a first side of the optical measurement chamber, across the extent of the measurement chamber and through the transparent sidewall on the other side of the optical measurement chamber. Positioned in optical proximity to the transparent sidewalls of the measurement chamber is a second mirror, angled at a 45° angle to the plane of the transparent sidewalls, wherein the mirror is either exposed to or covered by an optically-transparent portion of the surface of the platform. Light emitted through the transparent sidewall of the optical measurement chamber is reflected by the second mirror perpendicularly to the surface of the rotor or microsystem platform and onto a photosensitive light collector, for example, a photoelectric cell, a photodiode or a photomultiplier tube calibrated to measure the absorbance or % transmittance of the reflected light.

The mirrors of this embodiment of the invention can either be manufactured and embedded in the surface of the rotor or platform, or the surfaces of the platform or rotor comprising the mirrors can be integrally molded and metallicized in plastic.

It will be understood that the foregoing discussion emphasizes certain specific embodiments of the invention and that all modifications or alternatives equivalent thereto are within the spirit and scope of the invention as set forth herein.

What is claimed is:

1. In a centripetally-motivated fluid micromanipulation apparatus, a microsystem platform comprising
  a) a rotatable platform, comprising a substrate having a first flat, planar surface and a second flat, planar surface opposite thereto, each surface comprising a center about which the platform is rotated, wherein the first surface comprises in combination
  b) an entry port comprising a depression in the first surface having a volumetric capacity of about 1 to about 150 µL, that is in direct fluid communication with
  c) a first metering capillary and a second overflow capillary, each being indirect fluid communication with the entry port, wherein each capillary defines a cross-sectional dimension of about 0.02 mm to about 1 mm, and wherein each capillary extends radially from the center of the platform and defines a first end proximally arrayed towards the center of the platform and a second end distally arrayed from the center of the platform, wherein the proximal end of each capillary defines a curved opening; wherein the first metering capillary defines a volume of the fluid and wherein the first metering capillary is fluidly connected with
  d) a first fluid chamber having a depth in the first surface of the platform equal to or greater than the metering capillary and positioned radially more distant from the center of the platform than the entry port, and the second overflow capillary is fluidly connected with
  e) an overflow chamber having a depth in the surface of the platform equal to or greater than the overflow capillary and positioned radially more distant from the center of the platform than the first fluid chamber and the entry port,
    wherein a capillary junction is formed between each of the metering capillary and the first fluid chamber and the overflow capillary and the overflow chamber, whereby fluid placed onto the disk at the entry port flows by capillary action to the junction of the metering capillary and the first fluid chamber, and excess fluid flows by capillary action to the junction of the overflow capillary and the overflow chamber; and wherein rotation of the platform at a first rotation speed motivates fluid displacement in the overflow capillary into the overflow chamber but not fluid displacement in the metering capillary, whereby rotation of the platform at the first rotational speed drains the fluid from the entry port into the overflow chamber; and
    wherein rotation of the platform at a second rotation speed that is greater than the first rotational speed motivates fluid displacement of the volume of the fluid in the metering capillary into the first fluid chamber; and wherein each of the first and overflow chambers also comprise air displacement channels whereby air displaced by fluid movement is vented to the first surface of the platform.

2. A method for moving a fluid in a microsystem platform according to claim 1, the method comprising the steps of
  a) applying an amount of a fluid sample comprising a volume of about 1 to about 100 µL to the entry port of the rotatable microsystem platform;
  b) rotating the platform at a first rotation speed for a time sufficient to displace the fluid in the entry port and the overflow capillary into the overflow chamber;
  c) rotating the platform at a second rotation speed that is greater than the first rotational speed displace a volume of the fluid in the metering capillary into the first fluid chamber.

* * * * *